US007666987B2

(12) United States Patent
O'Brien et al.

(10) Patent No.: US 7,666,987 B2
(45) Date of Patent: Feb. 23, 2010

(54) BIOLUMINESCENT CASPASE ASSAY COMPOUNDS

(75) Inventors: Martha O'Brien, Madison, WI (US); Keith V. Wood, Mt. Horeb, WI (US); Dieter Klaubert, Arroyo Grande, CA (US); William Daily, Santa Maria, CA (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 11/347,054

(22) Filed: Feb. 3, 2006

(65) Prior Publication Data

US 2006/0121546 A1 Jun. 8, 2006

Related U.S. Application Data

(62) Division of application No. 10/356,665, filed on Jan. 31, 2003, now Pat. No. 7,148,030.

(60) Provisional application No. 60/353,158, filed on Feb. 1, 2002.

(51) Int. Cl.
*C07K 1/00* (2006.01)
(52) U.S. Cl. .......................... 530/335; 435/8
(58) Field of Classification Search ................. 530/335; 435/8
See application file for complete search history.

(56) References Cited

U.S. PATENT DOCUMENTS

| | | | |
|---|---|---|---|
| 4,557,862 A | 12/1985 | Mangel et al. | |
| 4,640,893 A | 2/1987 | Mangel et al. | |
| 5,035,999 A * | 7/1991 | Geiger et al. ................. | 435/23 |
| 5,098,828 A | 3/1992 | Geiger et al. | |
| 5,314,805 A | 5/1994 | Haugland et al. | |
| 5,698,411 A | 12/1997 | Lucas et al. | |
| 5,744,320 A | 4/1998 | Sherf et al. | |
| 5,834,196 A | 11/1998 | Reutelingsperger | |
| 5,976,822 A | 11/1999 | Landrum et al. | |
| 6,251,614 B1 | 6/2001 | Fritz et al. | |
| 6,270,980 B1 | 8/2001 | Fritz et al. | |
| 6,335,429 B1 | 1/2002 | Cai et al. | |
| 6,586,196 B1 | 7/2003 | Bronstein et al. | |
| 6,602,657 B1 | 8/2003 | Bronstein et al. | |
| 6,613,541 B1 | 9/2003 | Vaddi et al. | |
| 6,759,207 B2 | 7/2004 | Weber et al. | |
| 6,811,990 B1 | 11/2004 | Corey et al. | |
| 6,890,745 B1 * | 5/2005 | Leng ............................. | 435/189 |
| 7,148,030 B2 * | 12/2006 | O'Brien et al. ................. | 435/8 |
| 7,384,758 B2 | 6/2008 | O'Brien et al. | |
| 7,416,854 B2 | 8/2008 | Riss et al. | |
| 2002/0068316 A1 | 6/2002 | Rust et al. | |
| 2002/0119500 A1 | 8/2002 | Xue et al. | |
| 2003/0211560 A1 | 11/2003 | O'Brien et al. | |
| 2004/0171099 A1 | 9/2004 | Cali et al. | |
| 2005/0164321 A1 | 7/2005 | Riss et al. | |
| 2006/0183177 A1 | 8/2006 | O'Brien et al. | |
| 2007/0178545 A1 | 8/2007 | Niles et al. | |
| 2008/0268482 A1 | 10/2008 | Riss et al. | |
| 2009/0017482 A1 | 1/2009 | Riss et al. | |

FOREIGN PATENT DOCUMENTS

| | | |
|---|---|---|
| AU | 199878177 | 12/1998 |
| EP | 1382691 A2 | 1/2004 |
| JP | 01-502431 | 8/1989 |
| WO | WO-88/05434 A1 | 7/1988 |
| WO | WO-00/36098 A1 | 6/2000 |
| WO | WO-00/50630 A2 | 8/2000 |
| WO | WO-0052194 A2 | 9/2000 |
| WO | WO-01/46694 A2 | 6/2001 |
| WO | WO-01/57242 A2 | 8/2001 |
| WO | WO-02/00882 A2 | 1/2002 |
| WO | WO-02/006458 A2 | 1/2002 |
| WO | WO-02/12547 A1 | 2/2002 |
| WO | WO-03/025192 A2 | 3/2003 |
| WO | WO03/066611 A1 | 8/2003 |
| WO | WO-2005/073722 A2 | 8/2005 |
| WO | WO-2007/027653 A1 | 3/2007 |
| WO | WO-2008/127677 A2 | 10/2008 |
| WO | WO-2008/127677 A9 | 10/2008 |

OTHER PUBLICATIONS

"Apo-ONE Homogeneous Caspase-3/7 Assay", *Promega Online Catalog*, www.promega.com, 2 pages.
"Apo-ONE tm Homogeneous Caspase-3/7 Assay", *Promega Technical Bulletin No. 295*, (Part # TB295), (May, 2001), 12 pgs.
"CleavaLite tm: New Bioluminescent Caspase-3 Activity Assay", *Chemicon International Communications Update*, vol. 11, No. 2, (published before May 16, 2001), 1 pg.
"New Products—ApoAlert tm CPP32 Protease Assay Kits", *CLONTECHniques*, (Jan. 1997), 4-6.
"UniCAP Tryptase", http://www.labspec.co.za/tryptase.html, (Jan. 2002), 6 pages.
Armstrong, Robert C., et al., "Activation of the CED3/ICE-Related Protease CPP32 in Cerebellar Granule Neurons Undergoing Apoptosis But Not Necrosis", *The Journal of Neuroscience*, 17(2), (Jan. 15, 1997), 553-562.

(Continued)

*Primary Examiner*—Ralph Gtiomer
(74) *Attorney, Agent, or Firm*—Michael Best & Friedrich LLP

(57) ABSTRACT

A sensitive bioluminescent assay to detect proteases including caspases is provided which employs an aminoluciferin or a carboxy-terminal protected derivative thereof covalently linked via a peptide bond to a substrate for a caspase or an aminoluciferin or a carboxy-terminal protected derivative thereof covalently linked via a peptide bond to a peptide substrate comprising aspartate that is specifically cleaved by a protease specific for the substrate.

13 Claims, 14 Drawing Sheets

OTHER PUBLICATIONS

B, Merrifield, "Solid Phase Synthesis", *Science, American Association for the Advancement of Science*, US, 232, (1986),341-347.

Fernandes-Alnemri, Teresa, et al., "In vitro activation of CPP32 and Mch3 by Mch4, a novel human apoptotic cysteine protease containing two FADD-like domains", *Proceedings of NAS USA*, 93, (Jul. 1996), 7464-7469.

Garcia-Calvo, Margarita, et al., "Purification and catalytic properties of human caspase family members.", *Cell Death & Differentiation*, 6(4), (1999),362-369.

Los, Marek, et al., "Requirement of an ICE/CED-3 Protease for Fas/APO-1-Mediated Apoptosis", *Nature*, 375, (May 4, 1995),91-93.

Masuda-Nishimura, I., et al., "Development of a rapid positive/absent test for coliforms using sensitive bioluminescence assay", *Letters in Applied Microbiology*, 30, (2000), 130-135.

Miska, Werner, et al., "A New Type of Ultrasensitive Bioluminogenic Enzyme Substrates", *Biol. Chem. Hoppe-Seyler*, (May, 1988),407-411.

Miska, Werner, et al., "Synthesis and Characterization of Luciferin Derivatives for Use in Bioluminescence Enhanced Enzyme Immunoassays", *Journal of Clinical Chemistry and Clinical Biochemistry*, 25, (1987),23-30.

Monsees, Thomas, et al., "A Novel Bioluminogenic Assay for a-Chymotrypsin", *Journal of Bioluminescence and Chemiluminescence*, 10, (1995),213-218.

Monsees, Thomas, et al., "Synthesis and Characterization of a Bioluminogenic Substrate for a-Chymotrypsin", *Analytical Biochemistry*, 221, (1994),329-334.

Nicholson, Donald W., et al., "Identification of inhibition of the ICE/CED-3 protease necessary for mammalian apoptosis", *Nature*, 376, (Jul. 1995),37-43.

Ranjit, G. B., et al., "Poly(adenosine diphosphoribose) Polymerase in Peripheral Blood Leukocytes From Normal Donors and Patients With Malignancies", *Clinical Cancer Research*, 1(2), (1995), 223-234.

Schulz, Jorg B., et al., "Potassium Deprivation-Induced Apoptosis of Cerebellar Granule Neurons: A Sequential-Requirement for New mRNA and Protein Synthesis, ICE-Like Protease Activity, and Reactive Oxygen Species", *The Journal of Neuroscience*, 16(15), (1996),4696-4706.

T. Monsees, et al., "A Novel Bioluminogenic Assay for Alpha-Chymotrypsin", *Journal of Bioluminescence and Chemiluminescence*, 10, Coupled Alpha-Chymotrypsin Assay Abstract, England,(1995),213-218.

T, Monsees, et al., "Synthesis and Characterization of a Bioluminogenic Substrate for Alpha-Chymotrypsin", *Analytical Biochemistry*, 221, Coupled Alpha-Chymotrypsin Assay Abstract,(1994),329-334.

Tewari, Muneesh, et al., "Yama/CPP32b, a Mammalian Homolog of CED-3, Is a CrmA-Inhibitable Protease That Cleaves the Death Substrate Poly(ADP-Ribose) Polymerase", *Cell*, 81, (Jun. 1995),801-809.

Thornberry, N A., et al., "A combinatorial approach defines specificities of members of the caspase family and granzyme B. Functional relationships established for key mediators of apoptosis", *Journal of Biological Chemistry*, 272(29), (Jul. 18, 1997), 17907-11.

Thornberry, Nancy A., et al., "A novel heterodimeric cysteine protease is required for interleukin-1b processing in monocytes", *Nature*, 356, (Apr. 1992),768-774.

White, Emil H., et al., "Amino Analogs of Firefly Luciferin and Biological Activity Thereof", *Journal of the American Chemical Society*, 88 (7), (1966),2015-2019.

Y. Chang H., et al., "Proteases for Cell Suicide: Functions and Regulation of Caspases", *Microbiology and Molecular Biology Reviews: MMBR*. United States, 46, (2000),821-846.

"U.S. Appl. No. 10/356,665, Response filed Nov. 10, 2005 to Non-Final Office Action mailed Aug. 12, 2005", 18 pgs.

"U.S. Appl. No. 10/356,665, Non Final Office Action mailed Aug. 12, 2005", 7 pgs.

"U.S. Appl. No. 10/356,665, Notice of Allowance mailed Jan. 25, 2006", 7 pgs.

"U.S. Appl. No. 10/356,665, Restriction Requirement mailed Jun. 07, 2003", 7 pgs.

"U.S. Appl. No. 10/356,665, Supplemental Preliminary Amendment and Response filed Jun. 29, 2005 to Restriction Requirement mailed Jun. 07, 2003", 14 pgs.

"U.S. Appl. No. 11/346,043, Amendment and Response filed Dec. 17, 2007 to Office Action mailed Nov. 5, 2007", 11 pgs.

"U.S. Appl. No. 11/346,043, Amendment filed Apr. 28, 2008 to Notice of Allowance mailed Jan. 28, 2008", 3 pgs.

"U.S. Appl. No. 11/346,043, Non-Final Office Action mailed Nov. 5, 2007", 8 pgs.

"U.S. Appl. No. 11/346,043, Notice of Allowance mailed Jan. 28, 2008", 6 pgs.

"U.S. Appl. No. 11/346,043, Response filed Aug. 6, 2007 to Restriction Requirement mailed Jul. 6, 2007", 7 pgs.

"U.S. Appl. No. 11/346,043, Response filed Oct. 1, 2007 to Restriction Requirement mailed Aug. 31, 2007", 7 pgs.

"U.S. Appl. No. 11/346,043, Response to Rule 312 Communication filed May 1, 2008", 2 pgs.

"U.S. Appl. No. 11/346,043, Restriction Requirement mailed Jul. 6, 2007", 4 pgs.

"U.S. Appl. No. 11/346,043, Restriction Requirement mailed Aug. 31, 2007", 4 pgs.

"Australian Application Serial No. 2003216139, Examiner's First Report mailed Mar. 5, 2008", 4 pgs.

"Australian Application Serial No. 2003216139, Notice of Acceptance mailed Aug. 1, 2008", 11 pgs.

"Australian Application Serial No. 2003216139, Response filed Jul. 30, 2008 to Examiner's First Report mailed Mar. 5, 2008", 28 pgs.

"Canadian Application Serial No. 2,474,695, Voluntary Amendment mailed Jan. 25, 2008", 12 pgs.

"European Application Serial No. 03737580.5, Communication mailed Jan. 16, 2007", 3 pgs.

"European Application Serial No. 03737580.5, Response filed Jul. 26, 2007 to Communication mailed Jan. 16, 2007", 8 pgs.

"International Application Serial No. PCT/US03/02936, Amendment filed Feb. 3, 2004 to Written Opinion mailed Nov. 12, 2003", 16 pgs.

"International Application Serial No. PCT/US03/02936, International Preliminary Examination Report mailed Apr. 26, 2004", 18 pgs.

"International Application Serial No. PCT/US03/02936, International Search Report mailed Jul. 7, 2003", 4 pgs.

"International Application Serial No. PCT/US03/02936, Written Opinion mailed Sep. 24, 2003", 2 pgs.

"International Application Serial No. PCT/US03/02936, Written Opinion mailed Nov. 12, 2003", 6 pgs.

"Japanese Application Serial No. 2003-565985, Argument and Amendment filed Nov. 28, 2008 to Official Action mailed Jul. 1, 2008", 10 pgs.

"Japanese Application Serial No. 2003-565985, Official Action mailed Jul. 1, 2008", (English Translation), 4 pgs.

"Apoptosis Inducers And The Assay of Caspase Activity Biomol", *Fased Journal*, 2(8), Abstract No. T10, Federation of American Studies for Experimental Biology, (Apr. 24, 1998), p. A1488.

"Apoptosis: Annexin V & Propidium Iodide—Freedom to Discover", *Acumen Bioscience Ltd.*, (Prior to Jan. 20, 2004), 2 pgs.

"U.S. Appl. No. 10/762,836, Response filed Nov. 2, 2006 Non-Final Office Action mailed Sep. 8, 2006", 15 pgs.

"U.S. Appl. No. 10/762,836, Preliminary Amendment filed Aug. 31, 2007", 5 pgs.

"U.S. Appl. No. 10/762,836, Notice of Allowance mailed Mar. 25, 2008", 7 pgs.

"U.S. Appl. No. 10/762,836, Notice of Allowance mailed Nov. 7, 2007", 8 pgs.

"U.S. Appl. No. 10/762,836, Final Office Action mailed Feb. 2, 2007", 8 pgs.

"U.S. Appl. No. 10/762,836, Non-Final Office Action mailed Mar. 21, 2006", 16 pgs.

"U.S. Appl. No. 10/762,836, Non-Final Office Action mailed Sep. 8, 2006", 8 pgs.

"U.S. Appl. No. 10/762,836, Notice of Allowance mailed May 31, 2007", 6 pgs.

"U.S. Appl. No. 10/762,836, Response filed Apr. 2, 2007 Final Office Action mailed Feb. 2, 2007", 24 pgs.
"U.S. Appl. No. 10/762,836, Response filed Jun. 21, 2006 Non-Final Office Action mailed Mar. 21, 2006", 23 pgs.
"U.S. Appl. No. 11/489,978, Non-Final Office Action mailed Feb. 1, 2008", 13 pgs.
"U.S. Appl. No. 11/489,978, Notice of Allowance mailed Feb. 26, 2009", 5 pgs.
"U.S. Appl. No. 11/489,978, Notice of Allowance mailed Jul. 28, 2008", 9 pgs.
"U.S. Appl. No. 11/489/978, Response filed Dec. 21, 2007 to Restriction Requirement mailed Nov. 28, 2007", 7 pgs.
"U.S. Appl. No. 11/510,278, Non-Final Office Action mailed May 30, 2008", 13 pgs.
"U.S. Appl. No. 11/510,278, Restriction Reqiurement mailed Jan. 31, 2008", 8 pgs.
"U.S. Appl. No. 11/510,278, Response filed Nov. 26, 2008 to Non-Final Office Action mailed May 30, 2008", 18 pgs.
"U.S. Appl. No. 11/510,278, Response and Preliminary Amendment filed Mar. 3, 2008 to Restriction Requirement mailed Jan. 31, 2008", 8 pgs.
"U.S. Appl. No. 11/510,278, Non-Final Office Action mailed Jan. 22, 2009", 21 pgs.
"Beadlyte® Multiplex Assay Systems", *Product Guide, Upstate Cell Signalling Solutions*, (2002), 12 pgs.
"Caspase-Glo™ 3/7 Assay", *Technial Bulletin No. 323, Promega Corporation*, (May 2003), 13 pgs.
"Cell Cytotoxicity—Freedom to Discover", *Acumen Bioscience Ltd.*, (Prior to Jan. 20, 2004), 2 pgs.
"Cell Proliferation—Freedom to Discover", *Acumen Bioscience Ltd.*, (Prior to Jan. 22, 2004), 2 pgs.
"CellTiter-Blue™Cell Viability Assay", *Technical Bulletin No. 317, Promega Corporation*, (Dec. 2002), 12 pgs.
"CellTiter-Glo™ Luminescent Cell Viability Assay", *Technical Bullentin No. 288, Promega Corporation*, (May 2001), 11 pgs.
"CytoTox-ONE™ Homogeneous Membrane Integrity Assay", *Technical Bulletin No. 306, Promega Corporation*, (May 2003), 13 pgs.
"Dual-Light® Luminescent Report Gene Assay for Luciferase and Beta-Galactosidase", *Data Sheet, Applied Biosystems*, (2000), 2 pgs.
"European Application Serial No. 06790059.7, Communication mailed Sep. 23, 2008", 2 pgs.
"International Application No. PCT/US2005/002158, Partial International Search Report mailed Oct. 12, 2006", 2 pgs.
"International Application Serial No. PCT/US2005/002158, International Search Report mailed Jun. 14, 2007", 8 pgs.
"International Application Serial No. PCT/US2005/002158, Written Opinion mailed Jun. 14, 2007", 8 pgs.
"International Application Serial No. PCT/US2006/033622, International Search Report mailed Dec. 28, 2006", 6 pgs.
"International Application Serial No. PCT/US2006/033622, Written Opinion mailed Dec. 28, 2006", 7 pgs.
"International Application Serial No. PCT/US2008/004748, International Search Report mailed Nov. 7, 2008", 5 pgs.
"International Application Serial No. PCT/US2008/004748, Written Opinion mailed Nov. 7, 2008", 7 pgs.
"Japanese Application Serial No. 2003-565985, Office Action mailed Feb. 6, 2009", (w/ English Translation), 7 pgs.
"Japanese Application Serial No. 2003-565985, Amendment filed Jun. 8, 2009 to Official Action mailed Feb. 6, 2009" (w/ English Translation of Claims), 27 pgs.
"Multiplex Antibody Kits Custom Software & Hardware for Luminex tm", *MiraiBio Inc.*, (Prior to Jan. 20, 2004), 2 pgs.
Adrain, C., et al., "Apoptosis-Associated Release of Smac/DIABLO From Mitochondria Requires Active Caspases and is Blocked by Bcl-2", *The EMBO Journal*, 20(23), (2001), 6627-6636.
Batchlor, R. H. et al., "Use of cellular glucose-6-phosphate dehydrogenase for cell quantitation: applications in cytotoxicity and apoptosis assays", *Analytical Biochemistry*, 329(1), (2004), 35-42.
Berkers, C. R., et al., "Activity Probe for in vivo Profiling of the Specificity of Proteasome Inhibitor Bortezomib", *Nature Methods*, 2(5), (2005), 357-362.
Bond, J. S., et al., "Intracellular Proteases", *Annual Review of Biochemistry*, 56, (1987), 333-364.

Bronstein, I., et al., "Combined Luminescent Assays for Multiple Enzymes", *Bioluminescence and Chemiluminescence: Molecular Reporting With Photons*, (International Symposium Proceedings), (1997), 451-457.
Constam, D. B., et al., "Purumycin-Sensitive Aminopeptidase", *The Journal of Biological Chemistry*, 270(45), (1995), 36931-36939.
Cook, J. A., et al., "Viability Measurements in Mammalian Cell Systems", *Analytical Biochemistry*, 179, (1989), 1-7.
Damour, Marc, et al., "Non-Radioactive Multiplex Kinase Activity Assay Using Beadlyte® Suspension Microarrays", (Prior to Jan. 20, 2004), 1 pg.
De Jager, Wilco, et al., "Simultaneous Detection of 15 Human Cytokines in a Single Sample of Stimulated Peripheral Blood Mononuclear Cells", *Clinical and Diagnostic Laboratory Immunology*, 10(1), (2003), 133-139.
Dyer, Benjamin, et al., "A Noncommercial Dual Luciferase Enzyme Assay System for Report Gene Analysis", *Analytical Biochemistry*, 282, (2000), 158-161.
Farfan, A., et al., "Frequently Asked Questions Cytotox-One™ Homogeneous Membrane Integrity Assay", *Cell Notes*, Issue 6, (2003), 19-20.
Fenteany, G, et al., "Inhibition of proteasome activities and subunit-specific aminoterminal threonine modification by lactacystin", *Science*, 268(5211), (1995), 726-731.
Fernandez, Y., et al., "Differential Regulation of Noxa in Normal Melanocytes and Melanoma Cells by Proteasome Inhibition: Therapeutic Implications", *Cancer Research*, 65(14), (2005), 6294-6304.
Grant, et al., "Development of Novel Assays for Proteolytic Enzymes Using Rhodamine-Based Fluorogenic Substrates", *Journal of Biomolecular Screening*, 7(6), (2002), 531-540.
Gurtu, V., et al., "Fluorometric and Colorimetric Detection of Caspase Activity Associated with Apoptosis", *Analytical Biochemistry*, 251, (1997), 98-102.
Haunstetter, A., et al., "Apoptosis: Basic Mechanisms and Implications for Cardiovascular Disease", *Circulation Research*, 82, (1998), 1111-1129.
Karlsson, J. O, et al., "Proteolytic Activity in Intact Sheets of Polarized Epithelial Cells as Determined by a Cell-Permeable Fluorogenic Substrate", *Cell Biology International*, 24(4), (2000), 235-243.
Kisselev, et al., "The Caspase-Like Sites of Proteasomes,Their Substrate Specificity,New Inhibitors and Substrates,and Allosteric Interactions with the Trypsin-Like Sites", *The Journal of Biological Chemistry* vol. 278(38), (2003), 35869-35877.
Kisselev, A. F., et al., "Importance of the Different Proteolytic Sites of the Proteasome and the Efficacy of Inhibitors Varies With Protein Substrate", *The Journal of Biological Chemistry*, 281(13), (Mar. 31, 2006), 8582-8590.
Kisselev, A. F., et al., "Monitoring Activity and Inhibition of 26S Proteasomes With Fluorogenic Peptide Substrates", *Methods in Enzymology*, vol. 398, (2005), 364-378.
Liu, J., et al., "Visualizing and Quantifying Protein Secretion Using a Renilla Luciferase-GFP Fusion Protein", *Luminescence*, 15(1), (2000), 45-49.
Luker, G. D., et al., "Imaging 26S Proteasome Activity and Inhibition in Living Mice", *Nature Medicine*, 9(7), (2003), 969-973.
Mandlekar, S., et al., "Activation of Caspase-3 and c-Jun $NH_2$-terminal Kinase-1 Signaling Pathways in Tamoxifen-induced Apoptosis of Human Breast Cancer Cells", *Cancer Research*, 60, (2000), 5995-6000.
Martin, Chris S., "Dual Luminescence-Based Reporter Gene Assay for Luciferase and β-Galactosidase", *BioTechniques*, 21(3), (1996), 520-524.
Mellgren, R. L., et al., "Specificities of Cell Permeant Peptidyl Inhibitors for the Proteinase Activities of μ-Calpain and the 20 S Proteasome", *The Journal of Biological Chemistry*, 272(47), (1997), 29899-29903.
Myers, M. A., "Direct Measurement of Cell Numbers in Microtitre Plate Cultures Using the Fluorescent Dye SYBR Green", *Journal of Immunological Methods*, 212, (1998), 99-103.
Niles, A. L, et al., "A homogeneous assay to measure live and dead cells in the same sample by detecting different protease markers", *Analytical Biochemistry*, 366(2), (2007), 197-206.

Nolkrantz, Kerstin, et al., "Functional Screening of Intracellular Proteins in Single Cells in Patterned Cell Arrays Using Eletroporation", *Analytical Chemistry*, 74(16), (2002), 4300-4305.

O'Brien, M. A, et al., "Homogeneous Bioluminescent Protease Assays : Caspase-3 as a Model", *Journal of Biomolecular Screening*, 10(2), (2005), 137-148.

O'Connell, et al., "Live/Dead Assay for Cell Viability; AfCS Procedure Protocol PP00000023 (2002)", http://wwwsignaling-gateway.org/data/cgi-bin/ProtocolFile.cgi/afcs_PP00000023.pdf?pid=PP00000023, (2002), 1-5 pgs.

Ogbomo, H., et al., "NK sensitivity of neuroblastoma cells determined by a highly sensitive coupled luminescent method", *Biochemical and Biophysical Research Communications*, 339(1), (2006), 375-379.

Preta, G., et al., "Inhibition of Serine-Peptidase Activity Enhances the Generation of a Survivin-Derived HLA-A2-Presented CTL Epitope in Colon-Carcinoma Cells", *Scand J Immunol.*, 68(6), (Dec. 2008), 579-88.

Princiotta, et al., "Cells Adapted to the Proteasome Inhibitor 4-Hydroxy-5-Iodo-3-Nitrophenylacetyl-Leu-Leu-Leucinal-Vinyl Sulfone Require Enzymatically Active Proteasome for Continued Survival", *Proceeding of the National Academy of Sciences*, vol. 98(2), (2001), 513-519.

Qazi, Saara, et al., "A Novel Dual Reporter Assay for Studying Intracellular Bacterial Pathogens", *Luminescence*, 17, (Abstract Only), XIIth International Symposium on Bioluminescence and Chemiluminescence, (2002), p. 106.

Ramsby, M. L., "Differential Detergent Fractionation of Isolated Hepatocyes: Biochemical, Immunochemical and Two-Dimensional Gel Electrophoresis Characterization of Cytoskeletal and Noncytoskeletal Compartments", *Electrophoresis*, 15, (1994), 265-277.

Riss, T. L., et al., "Use of Multiple Assay Endpoints to Investigate the Effects of Incubation Time, Dose of Toxin, and Plating Density in Cell-Based Cytotoxicity Assays", *ASSAY and Drug Development Technologies*, 2(1), (Abstract Only), (2004), 1 pg.

Rosser, et al., "Calpain activity increases in hepatocytes following addition of ATP", *The Journal of Biological Chemistry*, vol. 268, No. 31, (1993), 23953-23600.

Sohnlein, Petra, et al., "Fast and Flexible Setup of Homogeneous Protein Assays Employing 6xHis-Tag Technology—High Sensitivity and Signal-to-Noise Ratios", (Qiagen (r) LiquiChip tm), (Published prior to Jan. 20, 2004), 13 pgs.

Syntichaki, P., et al., "The Biochemistry of Neuronal Necrosis: Rogue Biology?", *Nature Reviews*, 4, (2003), 672-684.

Timiryasova, T. M., et al., "Visualization of Vaccinia Virus Infection Using the Renilla-Luciferase-GFP Fusion Protein", *Bioluminescence and Chemiluminescence*, (11th International Proceedings), (2001), 457-460.

Tran, T. V., et al., "Dipeptidyl Peptidase I: Importance of Progranzyme Activation Sequences, Other Dipeptide Sequences, and the N-Terminal Amino Group of Synthetic Substrates for Enzyme Activity", *Archives of Biochemistry and Biophysics*, 403, (2002), 160-170.

Wang, Y., et al., "The Renilla Luciferase-Modified GFP Fusion Protein is Functional in Transformed Cells", *Bioluminescence and Chemiluminescence: Molecular Reporting with Photons*, (Symposium Proceedings,, (1997), 419-422.

Wilkinson, J. C., et al., "Upstream Regulatory Role for XIAP in Receptor-Mediated Apoptosis", *Molecular and Cellular Biology*, 24(16), (2004), 7003-7014.

Yu, Yong A., et al., "Inducible Gene Expression in Vivo Using a Renilla Luciferase—GFP Fusion Construct", *Bioluminescence and Chemiluminescence*, (11th International Symposium Proceedings), (2000), 465-468.

* cited by examiner

A.

B.

| Caspase | Recognition sites for cleavage | | |
|---|---|---|---|
| 1 | YVAD | WEHD | |
| 2 | VDVAD | DEHD | |
| 3 | DEVD | | |
| 4 | LEHD | WEHD | |
| 5 | LEHD | WEHD | |
| 6 | VEID | VEHD | VEVD |
| 7 | DEVD | | |
| 8 | IETD | LETD | (L/V)EXD |
| 9 | LEHD | | |
| 10 | AEVD | LEXD | |
| 11 | (I/L/V/P)EHD | | |

| Recognition Site | Caspase |
|---|---|
| YVAD | 1 |
| WEHD | 1, 4, 5 |
| VDVAD | 2 |
| DEHD | 2 |
| DEVD | 3, 7 |
| LEHD | 4, 5, 9, 11 |
| VEID | 6 |
| VEHD | 6, 11 |
| VEVD | 6 |
| IETD | 8 |
| LETD | 8 |
| LEXD | 8, 10 |
| VEXD | 8 |
| AEVD | 10 |
| IEHD | 11 |
| PEHD | 11 |

| Recognition Site | Caspase |
|---|---|
| AEVD | 10 |
| DEHD | 2 |
| DEVD | 3, 7 |
| IEHD | 11 |
| IETD | 8 |
| LEHD | 4, 5, 9, 11 |
| LETD | 8 |
| LEXD | 8, 10 |
| PEHD | 11 |
| VDVAD | 2 |
| VEID | 6 |
| VEHD | 6, 11 |
| VEVD | 6 |
| VEXD | 8 |
| WEHD | 1, 4, 5 |
| YVAD | 1 |

Figure 13

SEQUENCE LISTING

<160> NUMBER OF SEQ ID NOS: 19

<210> SEQ ID NO 1
<211> LENGTH: 4
<212> TYPE: PRT
<213> ORGANISM: Artificial Sequence
<220> FEATURE:
<223> OTHER INFORMATION: Recognition Site

<400> SEQUENCE: 1

Asp Glu Val Asp
 1

<210> SEQ ID NO 2
<211> LENGTH: 4
<212> TYPE: PRT
<213> ORGANISM: Artificial Sequence
<220> FEATURE:
<223> OTHER INFORMATION: Recognition Site

<400> SEQUENCE: 2

Tyr Val Ala Asp
 1

<210> SEQ ID NO 3
<211> LENGTH: 4
<212> TYPE: PRT
<213> ORGANISM: Artificial Sequence
<220> FEATURE:
<223> OTHER INFORMATION: Recognition Site

<400> SEQUENCE: 3

Leu Glu His Asp
 1

<210> SEQ ID NO 4
<211> LENGTH: 5
<212> TYPE: PRT
<213> ORGANISM: Artificial Sequence
<220> FEATURE:
<223> OTHER INFORMATION: Recognition Site

<400> SEQUENCE: 4

Val Asp Val Ala Asp
 1               5

<210> SEQ ID NO 5
<211> LENGTH: 4
<212> TYPE: PRT
<213> ORGANISM: Artificial Sequence
<220> FEATURE:
<223> OTHER INFORMATION: Recognition Site

<400> SEQUENCE: 5

Val Glu Ile Asp
 1

<210> SEQ ID NO 6
<211> LENGTH: 4
<212> TYPE: PRT
<213> ORGANISM: Artificial Sequence
<220> FEATURE:
<223> OTHER INFORMATION: Recognition Site

<400> SEQUENCE: 6

```
Ile Glu Thr Asp
 1

<210> SEQ ID NO 7
<211> LENGTH: 4
<212> TYPE: PRT
<213> ORGANISM: Artificial Sequence
<220> FEATURE:
<223> OTHER INFORMATION: Recognition Site

<400> SEQUENCE: 7

Ala Glu Val Asp
 1

<210> SEQ ID NO 8
<211> LENGTH: 4
<212> TYPE: PRT
<213> ORGANISM: Artificial Sequence
<220> FEATURE:
<223> OTHER INFORMATION: Recognition Site
<220> FEATURE:
<221> NAME/KEY: SITE
<222> LOCATION: 1
<223> OTHER INFORMATION: Xaa = Ile, Leu, Val, or Pro

<400> SEQUENCE: 8

Xaa Glu His Asp
 1

<210> SEQ ID NO 9
<211> LENGTH: 4
<212> TYPE: PRT
<213> ORGANISM: Artificial Sequence
<220> FEATURE:
<223> OTHER INFORMATION: Recognition Site

<400> SEQUENCE: 9

Trp Glu His Asp
 1

<210> SEQ ID NO 10
<211> LENGTH: 4
<212> TYPE: PRT
<213> ORGANISM: Artificial Sequence
<220> FEATURE:
<223> OTHER INFORMATION: Recognition Site

<400> SEQUENCE: 10

Asp Glu His Asp
 1

<210> SEQ ID NO 11
<211> LENGTH: 4
<212> TYPE: PRT
<213> ORGANISM: Artificial Sequence
<220> FEATURE:
<223> OTHER INFORMATION: Recognition Site

<400> SEQUENCE: 11

Val Glu His Asp
 1

<210> SEQ ID NO 12
<211> LENGTH: 4
<212> TYPE: PRT
<213> ORGANISM: Artificial Sequence
<220> FEATURE:
<223> OTHER INFORMATION: Recognition Site
```

```
<400> SEQUENCE: 12

Leu Glu Thr Asp
 1

<210> SEQ ID NO 13
<211> LENGTH: 4
<212> TYPE: PRT
<213> ORGANISM: Artificial Sequence
<220> FEATURE:
<223> OTHER INFORMATION: Recognition Site
<220> FEATURE:
<221> NAME/KEY: SITE
<222> LOCATION: 1
<223> OTHER INFORMATION: Xaa = Leu or Val
<220> FEATURE:
<221> NAME/KEY: SITE
<222> LOCATION: 3
<223> OTHER INFORMATION: Xaa = any amino acid

<400> SEQUENCE: 13

Xaa Glu Xaa Asp
 1

<210> SEQ ID NO 14
<211> LENGTH: 4
<212> TYPE: PRT
<213> ORGANISM: Artificial Sequence
<220> FEATURE:
<223> OTHER INFORMATION: Recognition Site
<220> FEATURE:
<221> NAME/KEY: SITE
<222> LOCATION: 3
<223> OTHER INFORMATION: Xaa = any amino acid

<400> SEQUENCE: 14

Leu Glu Xaa Asp
 1

<210> SEQ ID NO 15
<211> LENGTH: 4
<212> TYPE: PRT
<213> ORGANISM: Artificial Sequence
<220> FEATURE:
<223> OTHER INFORMATION: Recognition Site

<400> SEQUENCE: 15

Val Glu Val Asp
 1

<210> SEQ ID NO 16
<211> LENGTH: 4
<212> TYPE: PRT
<213> ORGANISM: Artificial Sequence
<220> FEATURE:
<223> OTHER INFORMATION: Recognition Site
<220> FEATURE:
<221> NAME/KEY: SITE
<222> LOCATION: 3
<223> OTHER INFORMATION: Xaa = any amino acid

<400> SEQUENCE: 16

Val Glu Xaa Asp
 1

<210> SEQ ID NO 17
<211> LENGTH: 4
<212> TYPE: PRT
<213> ORGANISM: Artificial Sequence
```

```
<220> FEATURE:
<223> OTHER INFORMATION: Recognition Site

<400> SEQUENCE: 17

Ile Glu His Asp
1

<210> SEQ ID NO 18
<211> LENGTH: 4
<212> TYPE: PRT
<213> ORGANISM: Artificial Sequence
<220> FEATURE:
<223> OTHER INFORMATION: Recognition Site

<400> SEQUENCE: 18

Pro Glu His Asp
1

<210> SEQ ID NO 19
<211> LENGTH: 4
<212> TYPE: PRT
<213> ORGANISM: Artificial Sequence
<220> FEATURE:
<223> OTHER INFORMATION: Recognition Site
<220> FEATURE:
<221> NAME/KEY: SITE
<222> LOCATION: 1
<223> OTHER INFORMATION: Xaa = Tyr, Asp, Leu, Val, Ile, Ala, Trp or Pro
<220> FEATURE:
<221> NAME/KEY: SITE
<222> LOCATION: 2
<223> OTHER INFORMATION: Xaa = Val or Glu
<220> FEATURE:
<221> NAME/KEY: SITE
<222> LOCATION: 3
<223> OTHER INFORMATION: Xaa = any amino acid

<400> SEQUENCE: 19

Xaa Xaa Xaa Asp
1
```

BIOLUMINESCENT CASPASE ASSAY COMPOUNDS

CROSS-REFERENCE TO RELATED APPLICATIONS

This application is a divisional of U.S. patent application Ser. No. 10/356,665, filed Jan. 31, 2003, now U.S. Pat. No. 7,148,030, which claims the benefit of the filing date of U.S. Provisional Patent Application Ser. No. 60/353,158, filed Feb. 1, 2002, under 35 U.S.C. § 119(e). The disclosures of which are incorporated by reference herein.

BACKGROUND OF THE INVENTION

Proteases constitute a large and important group of enzymes involved in diverse physiological processes such as blood coagulation, inflammation, reproduction, fibrinolysis, and the immune response. Numerous disease states are caused by, and can be characterized by, the alterations in the activity of specific proteases and their inhibitors. The ability to measure these proteases in research or clinically is significant to the investigation, treatment and management of disease states. For example, caspases 3 and 7 are members of the cysteine aspartyl-specific protease (also known as the aspartate specific-cysteine protease, "ASCP") family and play key effector roles in apoptosis in mammalian cells (Thornberry et al., 1992; Nicholson et al., 1995; Tewari et al., 1995; and Fernandes-Alnemri et al., 1996).

Proteases, however, are not easy to assay with their naturally occurring substrates. Moreover, many currently available synthetic substrates are expensive, insensitive, and nonselective. Furthermore, the use of high concentrations of the target protease, with either the naturally occurring substrate or a synthetic substrate, may be required for the assay, which may result in the self destruction of the protease.

Numerous chromogenic and fluorogenic substrates have been used to measure proteases (Monsees et al., 1994; Monsees et al., 1995) and modified luciferins have provided alternatives to fluorescent indicators (U.S. Pat. Nos. 5,035,999 and 5,098,828). Methods for using modified luciferins with a recognition site for a hydrolase as a pro-substrate were first described by Miska and Geiger (1989). These heterogenous assays were conducted by incubating the modified luciferin with a hydrolase for a specified period of time, then transferring an aliquot of the mixture to a solution containing luciferase. Masuda-Nishimura et al. (2000) reported the use of a single tube (homogenous) assay which employed a galactosidase substrate-modified luciferin. A non-heterogeneous luminescent protease assay has not yet been shown.

While luminescent assays are commonly known for their sensitivity, their performance relative to fluorescent assays is difficult to predict due to fundamental differences in assay formats. Specifically, enzyme-linked luminescence assays yield light coupled to the instantaneous rate of catalysis. In contrast, enzyme-linked fluorescence assays yield light based on the cumulative catalytic activity measured over a period of time (a so-called "endpoint" assay based upon accumulation of fluorophore). By integrating the catalytic activity over a period of time that can extend from hours to days, the light signal from a fluorescent assay can be greatly increased. Similar integration over such long periods is not practical for luminescent assays.

Thus, what is needed is a method to monitor protease activity that is a rapid, single-tube, homogeneous, sensitive assay.

SUMMARY OF THE INVENTION

The invention provides a sensitive luminescent method to detect a protease, e.g., a caspase, trypsin or tryptase. For instance, the invention provides a luminescent assay method to detect one or more caspases. The method comprises contacting a sample suspected of having one or more caspases with a mixture comprising beetle luciferase and an amino-modified beetle aminoluciferin or a carboxy-terminal protected derivative thereof, wherein the amino group of aminoluciferin or the derivative thereof is modified so as to covalently link a substrate for the caspase via a peptide bond to aminoluciferin or the carboxy-terminal protected derivative thereof. If the sample comprises a caspase having a recognition site in the substrate, the substrate is cleaved at the peptide bond that links the substrate to aminoluciferin, yielding aminoluciferin, a substrate for the luciferase, in the mixture. Luminescence is then detected. The method further comprises correlating luminescence with protease concentration or activity, i.e., increased luminescence correlates with increased protease concentration or activity. Preferably, the luminescent assay is more sensitive than a corresponding assay with a conjugate comprising a fluorophore covalently linked via an amide bond to at least one substrate molecule or a functional equivalent thereof. Thus, a conjugate comprising a fluorophore may be covalently linked to one or more molecules of the substrate. In one embodiment of the invention, the luminescent assay is more sensitive than a corresponding assay which employs the fluorophore rhodamine-110, which can be modified via an amide bond to link two protease substrates to the fluorophore.

A "functional equivalent" of a reference substrate is a substrate having one or more amino acid substitutions relative to the sequence of the reference substrate, which functionally equivalent substrate is recognized and cleaved by the same protease at a substantially similar efficiency as the reference substrate. FIG. 13 shows exemplary functionally equivalent substrates for various caspases.

The increased assay sensitivity with methods employing the luminescent substrates of the invention is at least 2 times, more preferably 3, 4, 5, 6, 7, 8, 9, or 10, or even greater, for instance, at least 15, 20, 25, 30, 40, 50, 100, 200, 500, or 1000 times or more, greater than that of an assay employing a conjugate comprising a fluorophore covalently linked to at least one substrate molecule or a functional equivalent thereof. Thus, the methods of the invention may detect less than 5 µU, or less, e.g., less than 1 µU, 0.5 µU or 0.2 µU of caspase in a sample. As used herein, the limit of detection means 3 standard deviations above background noise ("noise" is 1 standard deviation of background and background is a control without caspase).

As described hereinbelow, using a substrate for caspase 3 and 7 that was linked to either aminoluciferin or rhodamine-110, it was found that the limit of detection for the aminoluciferin-based substrate was 0.2 to 0.5 µU of purified caspase while that for the rhodamine-110-based substrate was 10 µU. As also described herein, it was found that the limit of detection of caspase expressing cells with the aminoluciferin-based substrate was 15 cells at 1 hour while the limit of detection for the rhodamine-110-based substrate was 150 cells at 1 hour. Thus, the methods of the invention may be employed with a sample comprising purified or partially-purified preparations of enzyme, as well as a sample comprising a cell lysate or intact cells. Moreover, due to the increased sensitivity of the assay of the invention, accurate background levels of activity, e.g., in resting cells such as those in the absence of inducer or toxin, can be readily and accurately established.

The invention also provides a luminescent assay method to detect a protease that specifically cleaves a substrate comprising aspartate. The method comprises contacting a sample suspected of having one or more aspartate-specific proteases with a mixture comprising luciferase and an amino-modified aminoluciferin or a carboxy-terminal protected derivative thereof, wherein the amino group of aminoluciferin or the derivative thereof is modified so as to covalently link the substrate via a peptide bond to aminoluciferin or a carboxy-terminal protected derivative thereof. If the sample comprises a protease having aspartate as a recognition site, the substrate is cleaved at the peptide bond that links the substrate comprising aspartate to aminoluciferin, yielding aminoluciferin, a substrate for the luciferase in the mixture. Then luminescence is detected in the sample. Preferably, the luminescent assay is more sensitive than a corresponding assay with a conjugate comprising a fluorophore covalently linked to one or more molecules of the substrate or a functional equivalent thereof. Preferred proteases that specifically cleave a substrate comprising aspartate include but are not limited to caspases, e.g., any one of caspases 1-14. Preferred substrates comprise $X_1$-$X_2$-$X_3$-D, (SEQ ID NO:19) wherein $X_1$ is Y, D, L, V, I, A, W, or P; $X_2$ is V or E; and $X_3$ is any amino acid, for instance, a substrate comprising DEVD (SEQ ID NO:1), WEHD (SEQ ID NO:9), VDVAD (SEQ ID NO:4), LEHD (SEQ ID NO:3), VEID (SEQ ID NO:5), VEVD (SEQ ID NO:15), VEHD (SEQ ID NO:11), IETD (SEQ ID NO:6), AEVD (SEQ ID NO:7), LEXD (SEQ ID NO:14), VEXD (SEQ ID NO:16), IEHD (SEQ ID NO:17), or PEHD (SEQ ID NO:18).

The invention also provides a luminescent assay method to detect trypsin or tryptase. The method comprises contacting a sample suspected of having trypsin or tryptase with a mixture comprising luciferase and an amino-modified aminoluciferase or a carboxy-terminal protected derivative thereof, wherein the amino group of aminoluciferin or the derivative thereof is modified so as to covalently link a substrate for trypsin or trytase via a peptide bond to aminoluciferin or a carboxy-terminal protected derivative thereof. Luminescence is then detected. Preferably, the luminescent assay is more sensitive than a corresponding assay with a conjugate comprising a fluorophore covalently linked to at least one substrate molecule or a functional equivalent thereof. For trypsin, arginine and lysine are functionally equivalent substrates as trypsin cleaves the peptide bond after those residues with substantially similar efficiencies. The increased assay sensitivity with methods employing the luminescent substrates of the invention for trypsin or tryptase is at least 2 times, more preferably 3, 4, 5, 6, 7, 8, 9, or 10, or even greater, for instance, at least 15, 20, 25, 30, 40, 50 or 100 times or more, greater than that of an assay employing a conjugate comprising a fluorophore covalently linked to at least one substrate molecule or a functional equivalent thereof. Using a substrate for trypsin, it was found that the limit of detection for a lysyl-aminoluciferin substrate was 3.0 pg while that for the arginine$_2$-rhodamine-110-based substrate was 12 to 30 pg. Thus, a trypsin assay which employs an amino-modified aminoluciferin substrate is at least 4 times more sensitive than a corresponding assay with a conjugate comprising rhodamine-110 covalently linked to two functionally equivalent trypsin substrates.

Further provided is a luminescent assay method to detect a protease that specifically cleaves a substrate comprising arginine or lysine. The method comprises contacting a sample suspected of having one or more proteases specific for a substrate comprising arginine or lysine with a mixture comprising luciferase and an amino-modified aminoluciferase or a carboxy-terminal protected derivative thereof covalently linked via a peptide bond to a substrate comprising arginine or lysine. Luminescence in the sample is then detected. Preferably, the assay is more sensitive than a corresponding assay with a conjugate comprising a fluorophore covalently linked to the substrate or a functional equivalent of the substrate. As tryptase is released from activated mast cells in association with inflammatory conditions including allergic reactions such as anaphylactic reactions and allergic rhinitis, and trypsin in stool may be indicative of cystic fibrosis, the methods of the invention may be of diagnostic use, or to monitor a mammal subjected to therapy, e.g., anti-inflammatory therapy.

Also provided is a compound comprising aminoluciferin or a carboxy-terminal protected derivative thereof covalently linked via a peptide bond to a protease recognition site such as a caspase recognition site, a trypsin recognition site, or a tryptase recognition site.

The invention also provides synthetic processes and intermediates disclosed herein, which are useful for preparing compounds of the invention.

Kits useful in the methods of the invention are also envisioned. Such kits may comprise the amino-modified aminoluciferins or carboxy-terminal protected derivatives of the invention, and instructions for their use, optionally a luciferase, for instance a thermostable luciferase and also optionally a buffer for a luminescence reaction which may include a lysing agent.

Aminoluciferin produces about 60% of the light output as luciferin under saturating conditions. The $K_m$ shifts from about 0.6 µM for luciferin to 2 µM for aminoluciferin.

Figure 1:
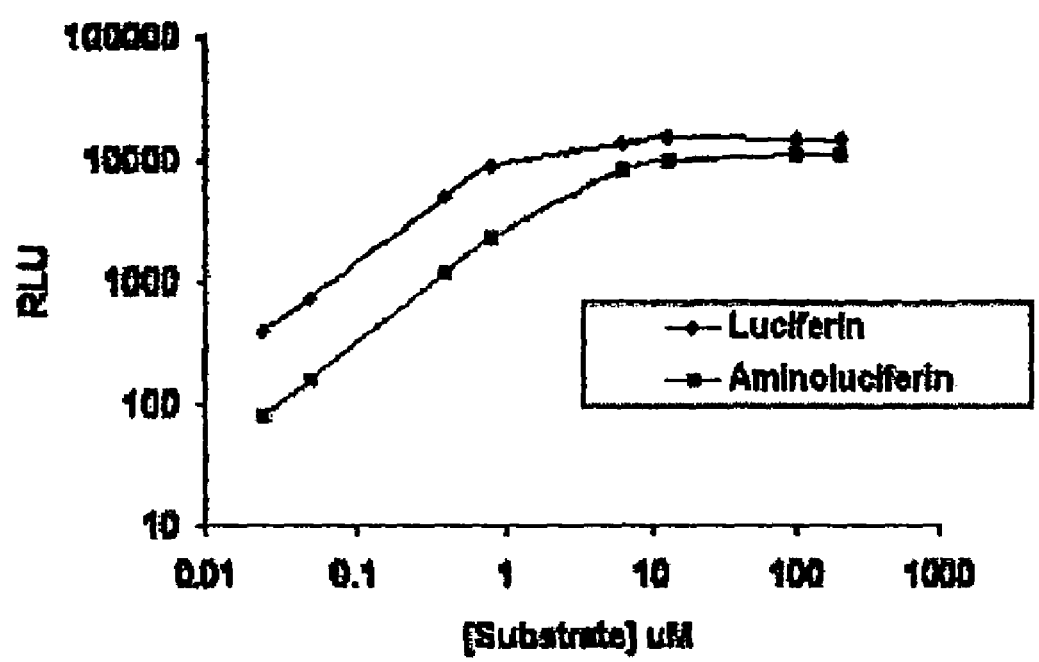
FIG. 1 depicts relative light units (RLU) for luciferin or aminoluciferin as a substrate for a thermostable firefly luciferase in a luminescent reaction.
Figure 2:
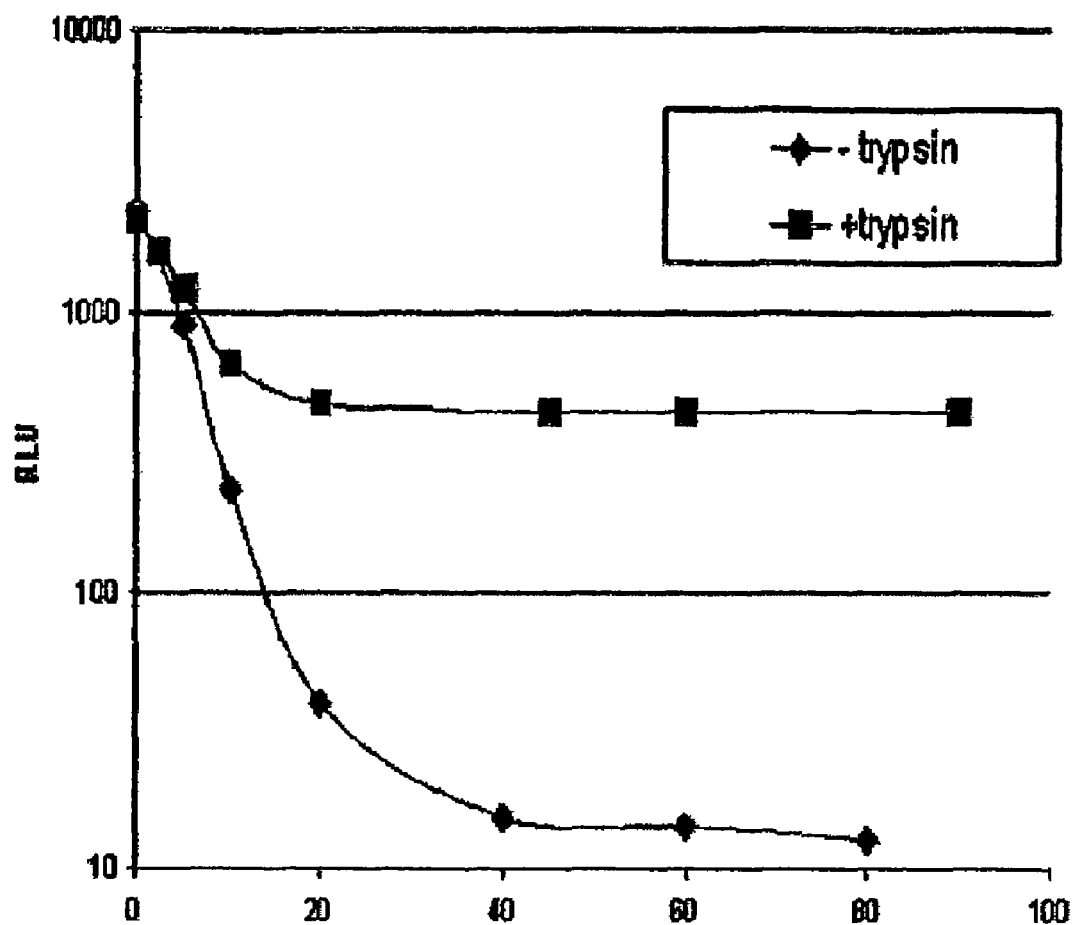

FIG. 2 illustrates the elimination of background signal from free aminoluciferin in a homogeneous assay format. Free aminoluciferin can produce high background signal even in the absence of trypsin. This background signal decreases as the free aminoluciferin is consumed by luciferase. By combining the substrate with luciferase, ATP, and Mg+ prior to the exposure to protease, the signal to noise ratio is dramatically increased. Moreover, the presence of the protease did not interfere with the luciferase reaction.

FIG. 3A shows RLU from a trypsin titration with N-Lys-aminoluciferin over time. Substrate was combined with luciferase, ATP, and Mg+ in buffer and incubated overnight to eliminate free aminoluciferin. The substrate mixture was then added to the trypsin titrations.

FIG. 3B shows RLU (log) from a trypsin titration with N-Lys-aminoluciferin over an extended period of time.

Figure 4:
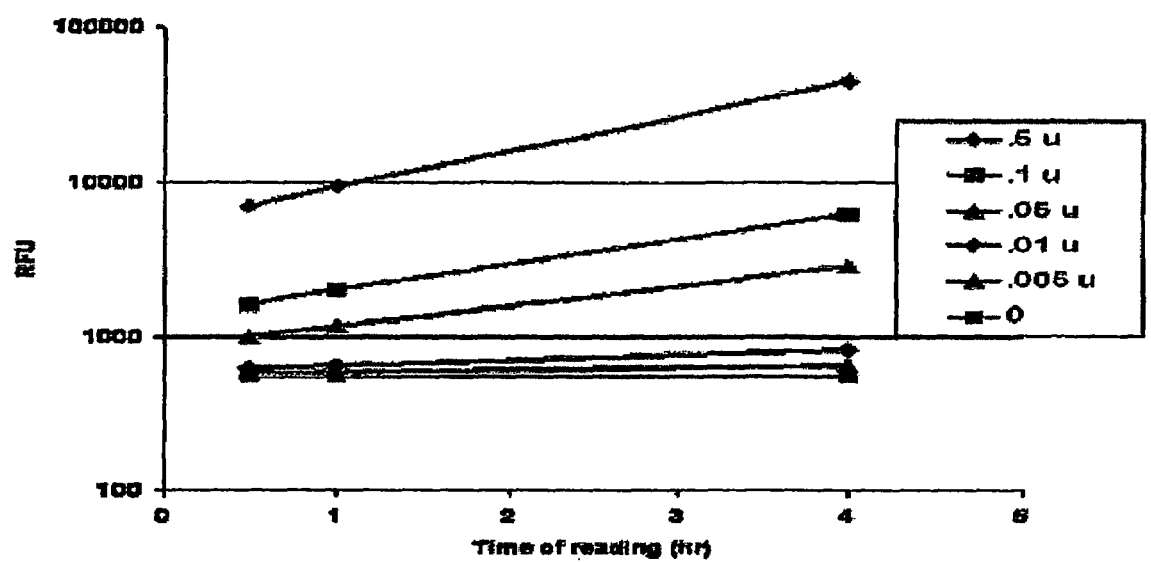

FIG. 4 depicts relative fluorescent units (RFU) from a trypsin titration with Z-Arg-Rho110.

Figure 5:
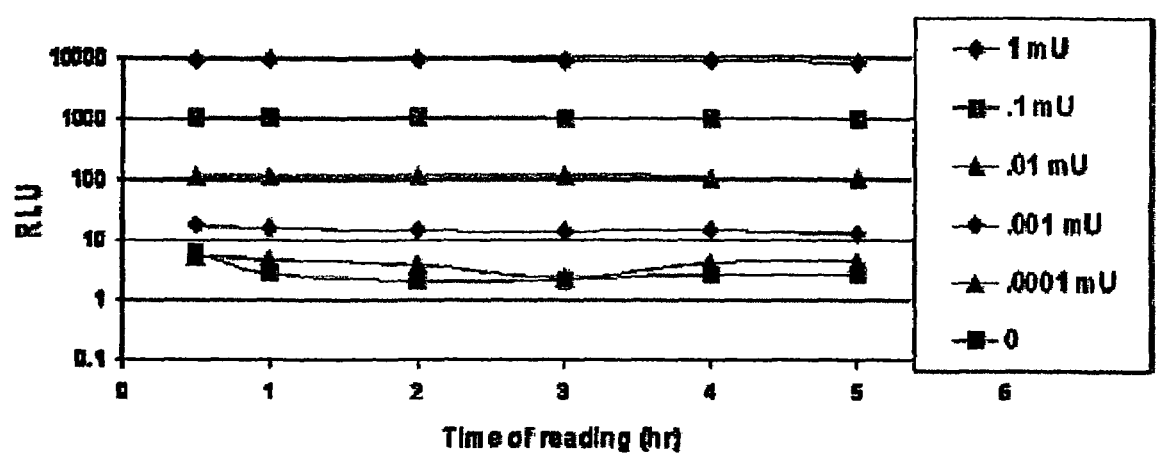

FIG. 5 shows RLU from a caspase titration with Z-DEVD-aminoluciferin over time. Luciferase, ATP, and Mg+ in buffer were added to the substrate.

Figure 6:
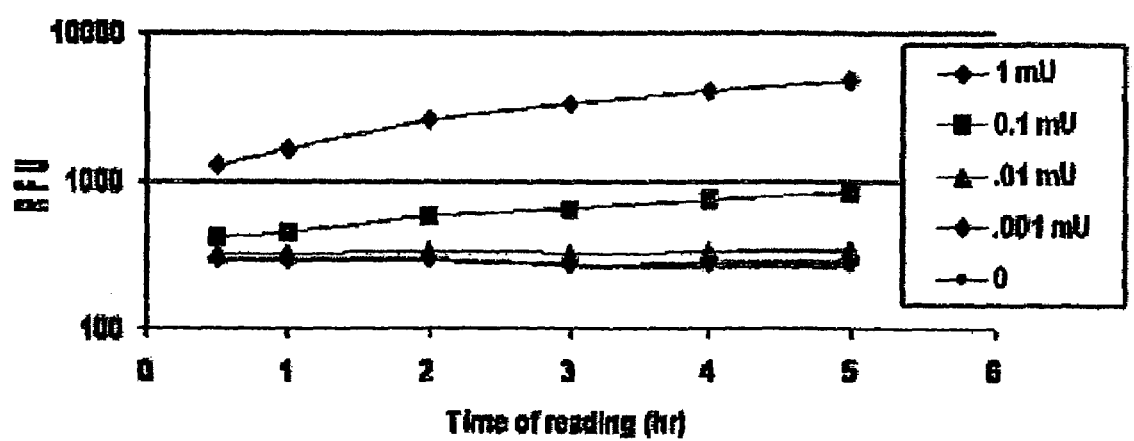

FIG. 6 shows RFU from a caspase titration with Z-DEVD-Rho110. The fluorescent Z-DEVD-Rho110 substrate was provided in the Apo-ONE™ Homogeneous Caspase 3/7

Assay kit (Promega). The same buffer was used for the DEVD-Rho110 substrate as for the DEVD-aminoluciferin substrate (see FIG. 5).

Figure 7:
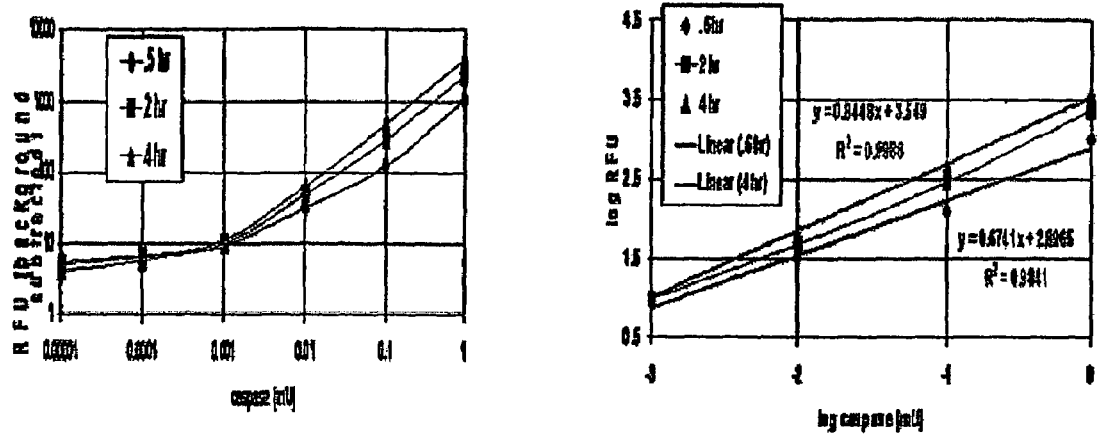

FIG. 7 shows RFU (background subtracted) or RFU (log) for caspase and Z-DEVD-Rho110.

Figure 8:
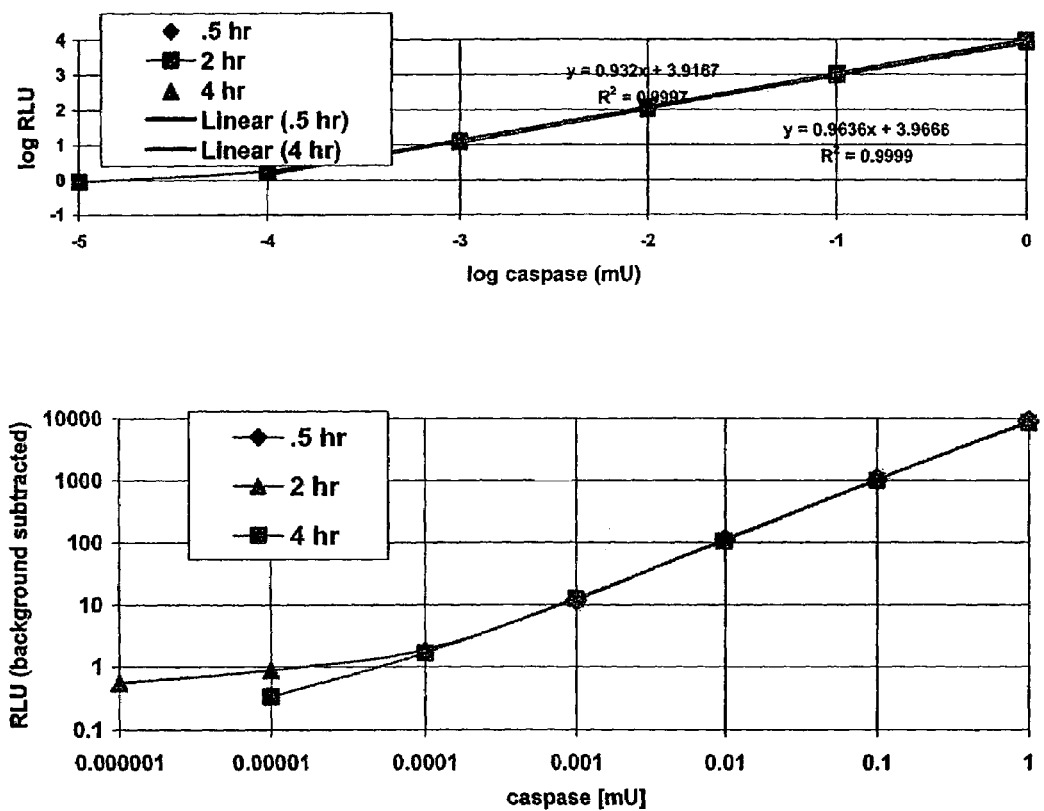

FIG. 8 shows RLU (background subtracted) or RLU (log) for caspase and Z-DEVD-aminoluciferin.

Figure 9:
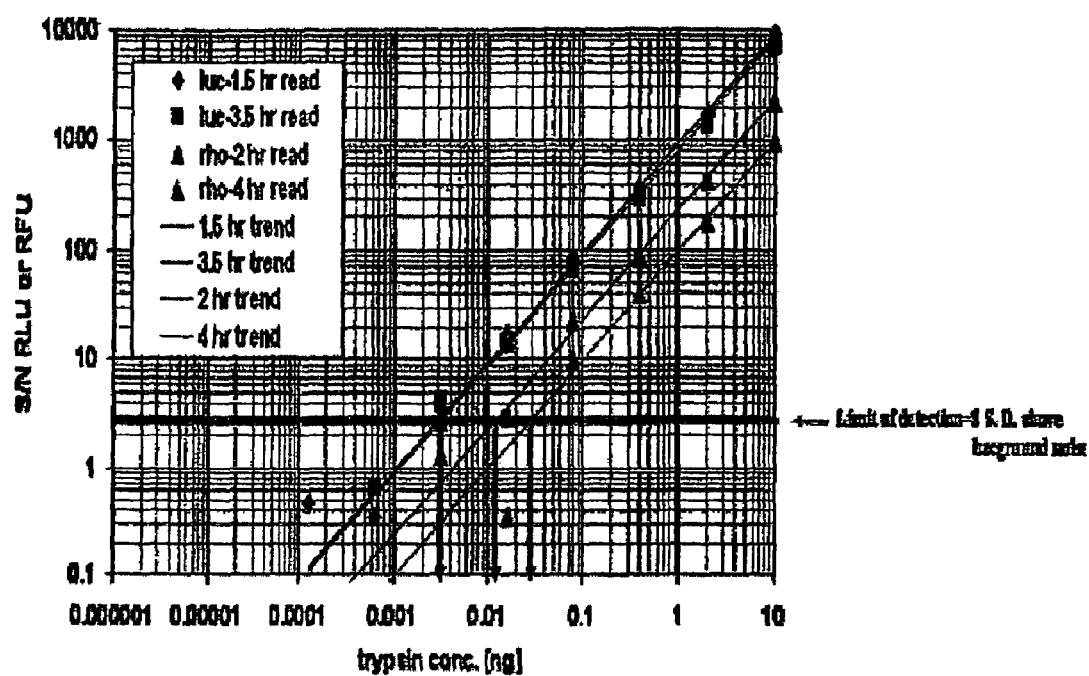

FIG. 9 is a comparison of RLU and RFU for trypsin with N-Lys-aminoluciferin or Z-Arg-Rho110 as a substrate. Trypsin titrations were set up as described above. The luminescent assay was more sensitive than a comparable fluorescent assay, e.g., the Lys-aminoluciferin substrate has a sensitivity 3-10 fold greater than the Arg-Rho110 depending on the time of the reading.

Figure 10:
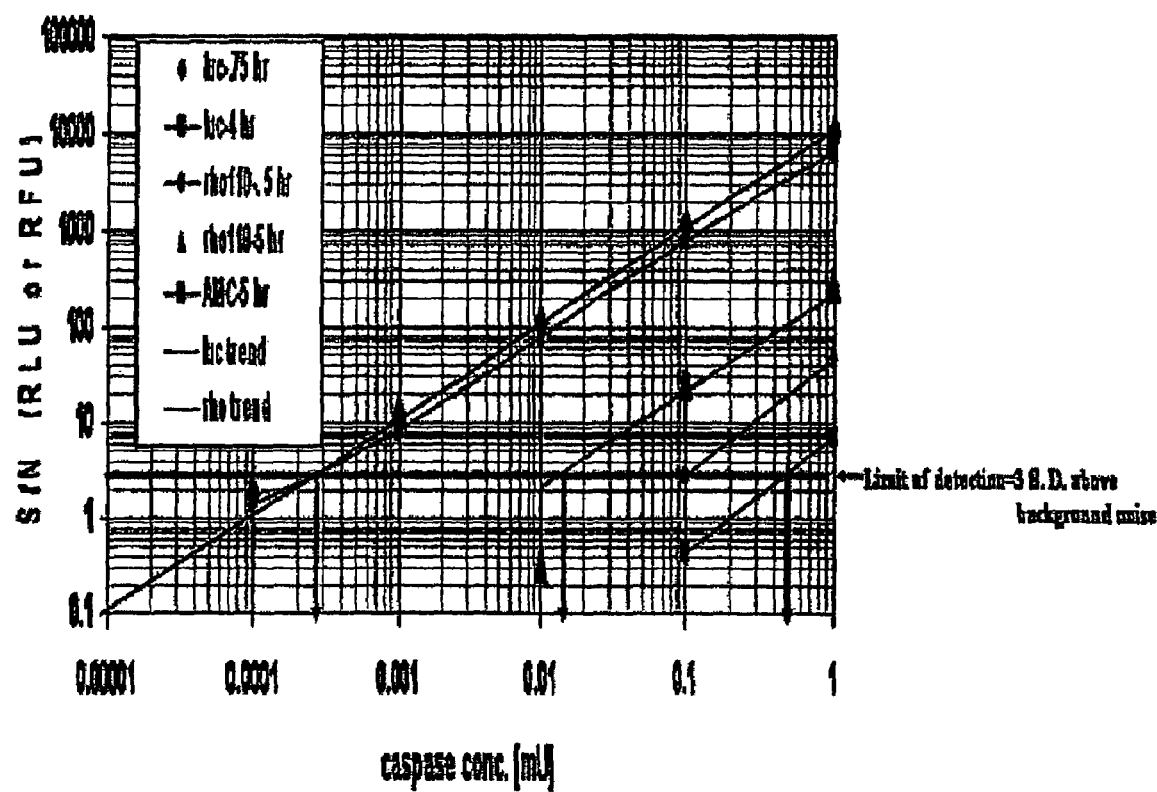

FIG. 10 is a comparison of RLU and RFU for caspase and Z-DEVD-aminoluciferin, Z-DEVD-AMC or Z-DEVD-Rho110 as a substrate. The Z-DEVD-Rho110 substrate and buffer used were the Apo-ONE™ (Promega) substrate and buffer. The same buffer was used for the DEVD-AMC substrate. The DEVD-aminoluciferin substrate had a sensitivity 50-300 fold greater than the Arg-Rho110 depending on the time of the readings.

Figure 11:
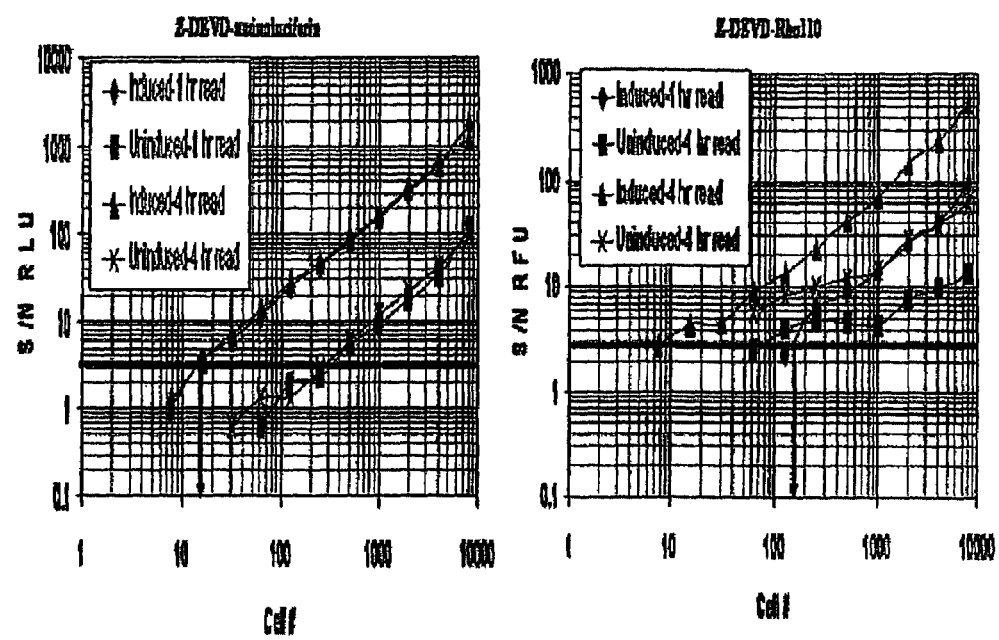

FIG. 11 shows RLU or RFU obtained with Jurkat cells (induced or uninduced) and the caspase substrate Z-DEVD-aminoluciferin or Z-DEVD-Rho110. The Apo-ONE™ buffer and Z-DEVD-Rho110 substrate were used for the fluorescent caspase assay. The same buffer was used for the DEVD-aminoluciferin substrate with the addition of luciferase, ATP, and MgSO$_4$. The DEVD-aminoluciferin substrate has a sensitivity 10-fold greater than the Arg-Rho110 at the 1 hour time point. At 4 hours, this decreased to about 2-fold.

Figure 12:
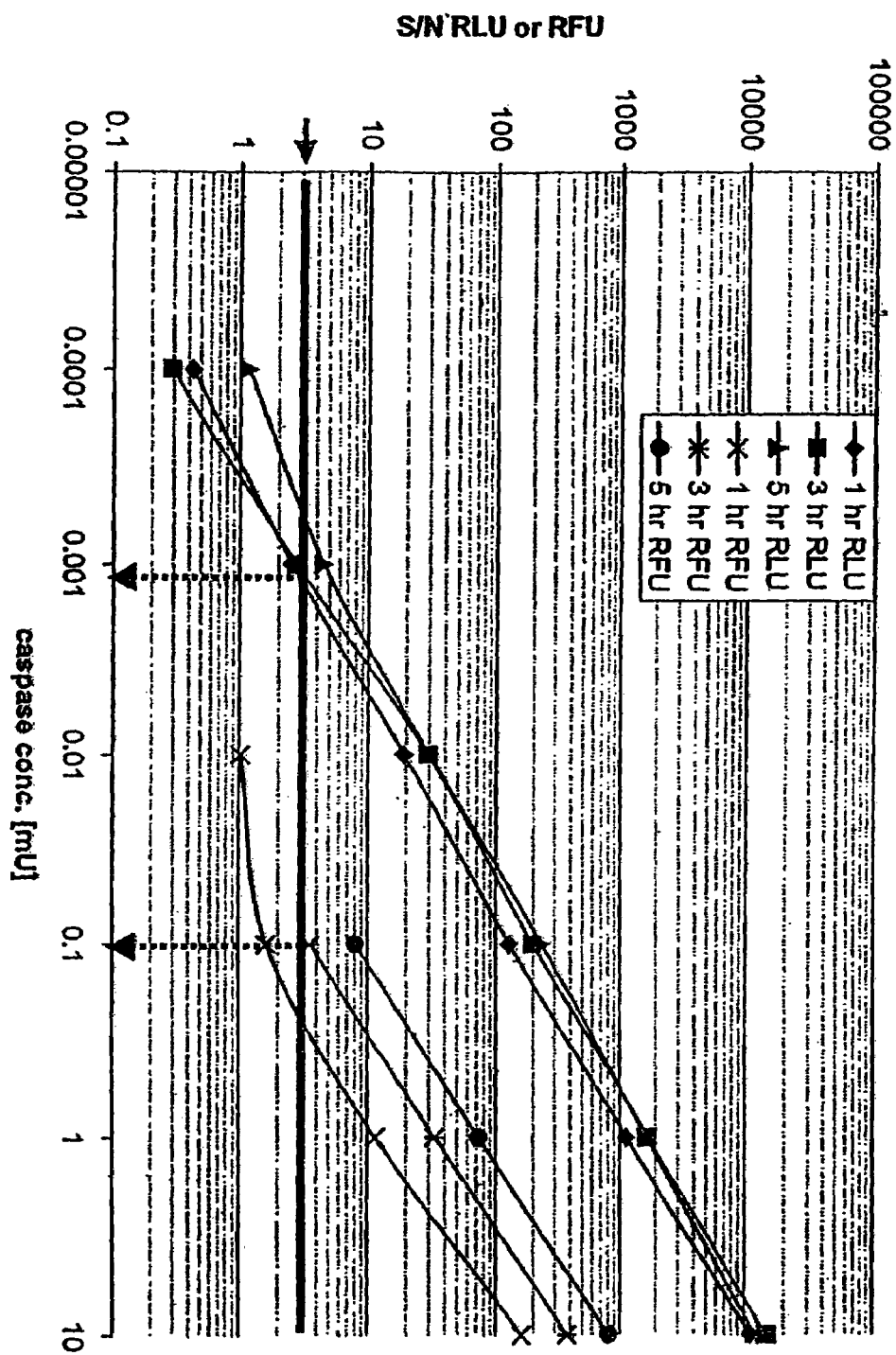
Figure 12:
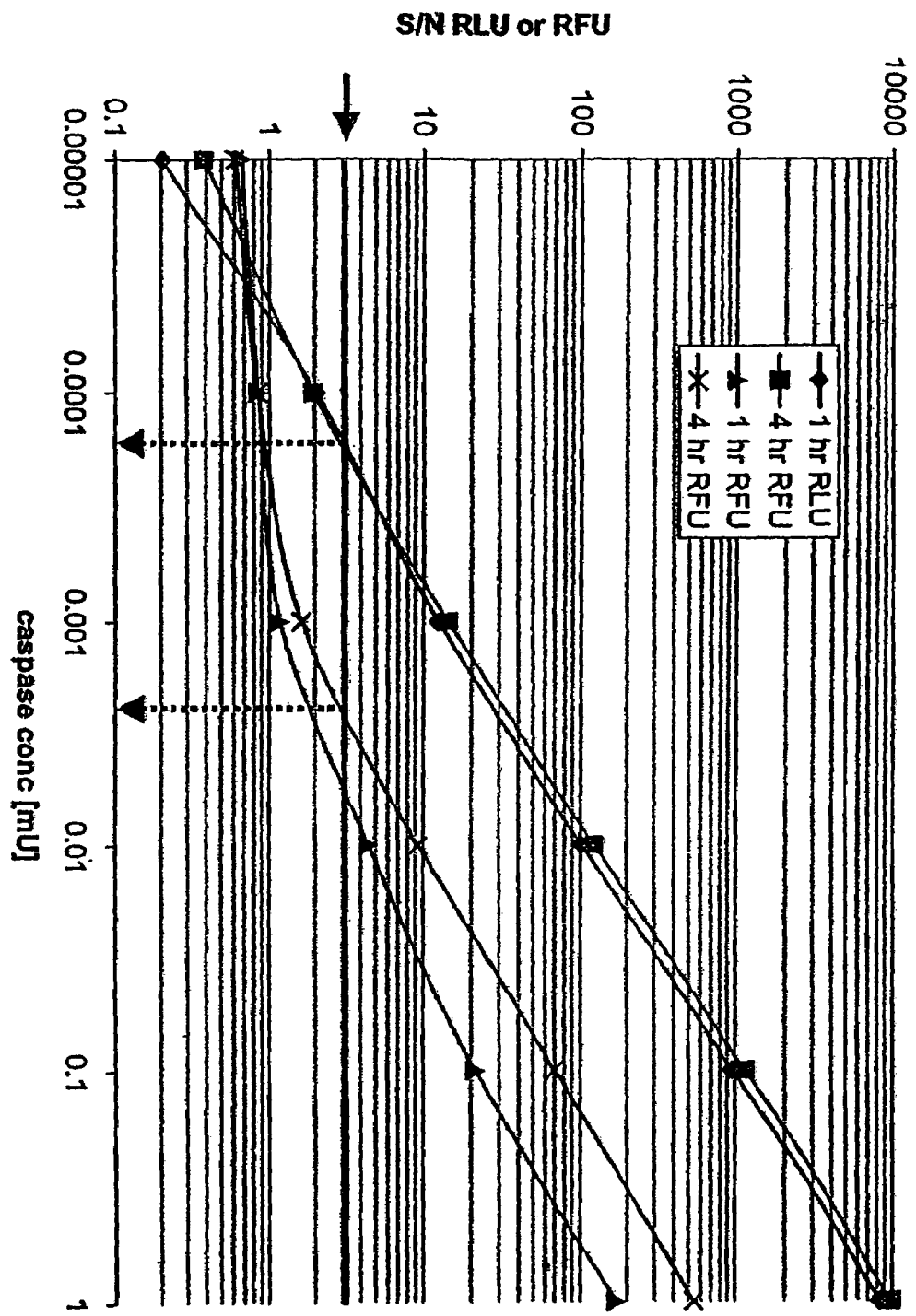

FIG. 12 shows relative RLU or RFU results obtained using CHAPS or Apo-ONE™ buffer.

FIG. 13 illustrates recognition sites for various caspases (SEQ ID NO: 1-18; Thornberry et al., 1997; Garcia-Calvo et al., 1999).

DETAILED DESCRIPTION OF THE INVENTION

Rapid and sensitive assays of proteolytic activity are important for general characterization of proteases and high-throughput screening for protease inhibitors. However, the inherent background of fluorescence, particularly in cell-based systems, can limit assay sensitivity. Moreover, to achieve maximum sensitivity, lengthy incubations are often required for accumulating the fluorescent assay product. Luminescent assays can often provide greater sensitivity in less time.

Thus, the present invention provides an improved, sensitive method for monitoring protease activity in purified preparations comprising the protease, in cell lysates or cells, either prokaryotic or eukaryotic cells. Preferred eukaryotic cells include mammalian cells, for example, human, feline, bovine, canine, caprine, ovine, swine, equine, non-human primate, e.g., simian, avian, plant or insect cells.

The cells may be cells that have not been genetically modified via recombinant techniques (nonrecombinant cells), or recombinant cells, the genome of which is augmented with a recombinant DNA. The DNA may encode a protease to be detected by the methods of the invention, a molecule which alters the level or activity of the protease in the cell, and/or a molecule unrelated to the protease or molecules that alter the level or activity of the protease.

The protease is detected using an amino-modified aminoluciferin or a carboxy-terminal protected derivative thereof, which modification comprises a substrate for the protease. The substrate, which comprises one or more amino acid residues which include the recognition site for the protease, is covalently linked to the amino group of aminoluciferin or the carboxy-terminal modified derivative via a peptide bond. Preferably, the N-terminus of the substrate is modified to prevent degradation by aminopeptidases, e.g., using an amino-terminal protecting group.

In the absence of the appropriate enzyme, a mixture comprising a substrate and luciferase will generate minimal light as minimal aminoluciferin is present (a small amount of light may be generated due to spontaneous hydrolysis of the peptide bond). In the presence of the appropriate enzyme, the peptide bond linking the substrate and aminoluciferin (the bond immediately adjacent to the 6' position on the luciferin core molecule) can be cleaved by the protease to yield aminoluciferin, a substrate for luciferase. Thus, in the presence of luciferase, for instance, a native, a recombinant or a mutant luciferase, light is generated, which is proportional to the amount or activity of the protease. Any beetle luciferase, preferably a thermostable luciferase, may be employed in the methods of the invention.

The aminoluciferin-based substrates of the invention are relatively inexpensive to synthesize and can be purified to high levels. Moreover, because they are extremely sensitive substrates, only very small amounts of a biological sample (e.g., cells, and physiological fluids, blood, urine, etc., which comprise cells) are required to perform the assay. Further, because the aminoluciferin-based substrates are extremely selective, little or no purification of the biological sample is required. For example, using such an assay, the activity of caspase 3, caspase 7 and trypsin was found to be below the level of detection of a corresponding assay using a Rhodamine-110 caspase substrate (Rhodamine-110 is likely one of the most sensitive indicators known). In particular, the sensitivity described herein for a caspase is superior to Apo-ONE™ (Promega, Madison, Wis.). Apo-ONE™ is a fluorescent based assay, which uses the fluorphore Rhodamine-110 conjugated to 2 recognition sequences for caspase 3/7.

Preferably, the methods of the invention are employed as a homogeneous assay for a protease, such as a caspase, tryptase or trypsin, i.e., the modified aminoluciferin, luciferase and additional components are mixed prior to adding the mixture to the sample. Results may be read without additional transfer of reagents.

A specific compound of the invention is a compound of formula (I):

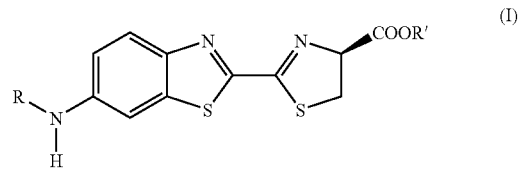

wherein R is a peptide that is a substrate for caspase, trypsin and tryptase, which is linked to the remainder of the compound of formula (I) through its C-terminus forming a peptide (amide) bond; and R' is H or a suitable carboxy protecting group (e.g. a (C$_1$-C$_6$)alkyl, phenyl or benzyl ester), or a suitable salt thereof.

Another specific compound of the invention is a compound of formula (I):

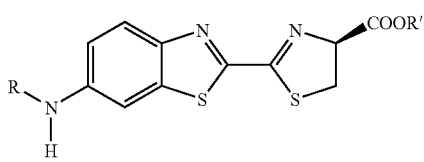

wherein R is a peptide that is linked to the remainder of the compound of formula (I) through an aspartate, lysine, or arginine group at the C-terminus of the peptide forming a peptide (amide) bond; and R' is H or a suitable carboxy protecting group (e.g. a ($C_1$-$C_6$)alkyl, phenyl or benzyl ester), or a suitable salt thereof.

It will be appreciated that salts of the amino-modified aminoluciferin compounds or the carboxy-terminal protected derivatives thereof can also be used in the methods described herein, and also form part of the invention. Methods for preparing suitable salts are known in the art.

Compounds of the invention can be prepared using procedures that are generally known, or they can be prepared using the procedures described herein. For example, compounds of the invention can be prepared using standard solution phase chemistry. Accordingly, a peptide can be coupled to an amino-cyanobenzothiazole, followed by reaction with D-cysteine to provide a compound of the invention. Alternatively, amino-cyanobenzothiazole can first be reacted with D-cysteine to provide an intermediate amino compound, which can subsequently be conjugated to a peptide to provide a compound of the invention.

Compounds of the invention can also be prepared using conventional solid-phase peptide synthesis techniques. For example, an aminoluciferin labeling reagent in the form of an N-protected amino acid that is attached to a peptide synthesis resin via the carboxylic acid function, can be prepared using standard coupling reagents (e.g., EDAC, DCC, or HOBt). The N-protective group is preferably Fmoc or t-Boc, but can be any group that can be removed without deleterious effect on the chemical bond connecting the label to the resin. Once attached to the resin the N-protective group is removed and the peptide is built onto the N-terminus of the resin-bound label using standard peptide synthesis protocols. At the end of peptide synthesis the labeled peptide is cleaved from the resin using standard cleavage reagents to provide the carboxylic acid.

Accordingly, the invention provides aminoluciferin coupled via the free carboxyl group to a solid support for the purposes of peptide synthesis. Such a carboxy-terminal protected aminoluciferin is convenient for the synthesis of a conjugate comprising a peptide of interest conjugated to the amino group of aminoluciferin. Preferably, the amino group is protected with an Fmoc or a t-Boc group.

The invention also provides a method for preparing a compound of the invention comprising forming an amide bond between the amino group of a solid support bound aminoluciferin and a first amino acid or a first peptide; and optionally attaching one or more additional amino acids or peptides through peptide bonds to provide the compound. The solid support bound aminoluciferin can optionally be prepared by attaching an N-protected aminoluciferin to a solid support through the carboxy group; and deprotecting the aminoluciferin. The support bound compound can then be removed to provide the corresponding free carboxylic acid, which can optionally be protected to provide a carboxyterminal protected derivative.

A carboxy-protected derivative of the invention can be prepared from the corresponding carboxylic acid using standard techniques. Accordingly, the invention provides a method to prepare a carboxy-terminal protected derivative of aminoluciferin, comprising protecting the corresponding acid with a suitable carboxy-protecting group.

Suitable amino protecting groups (e.g. Fmoc or t-Boc), as well as suitable carboxy protecting groups (e.g. ($C_1$-$C_6$)alkyl, phenyl or benzyl esters or amides) that can be incorporated into the compounds of the invention, are well known to those skilled in the art (See for example, T. W. Greene, *Protecting Groups In Organic Synthesis*; Wiley: New York, 1981, and references cited therein).

The invention will be further described by the following non-limiting examples.

EXAMPLE 1

To compare the limit of detection for a luminescence-based and a fluorescence-based assay for trypsin, two substrates, Lys-aminoluciferin (Cbz-modified lysinyl-aminoluciferin) and Arg-Rho-110 (Molecular Probes, Catalog no. R6501), were used. Substrate was resuspended in 100 mM Hepes, pH 7.9, at a concentration of 10 mM and stored at −20° C. The thawed Lys-aminoluciferin substrate, thermostable luciferase (5.2 mg/ml stock), and ATP (0.1 M stock) were diluted in buffer (50 mM HEPES, pH 7.9, 10 mM MgSO$_4$, 1 mM EDTA, pH 8.2 and 0.1% prionex) to make a stock that was 10× the final concentration. The 10× stock was 200 μM Lys-aminoluciferin, 200 μg/ml luciferase, and 2.0 mM ATP. This 10× stock was incubated for at least 90 minutes to eliminate any free aminoluciferin.

Trypsin was prepared for titration as follows: 1 μg/μl stock solution was diluted to 10 ng/50 μl in the same buffer as above (50 mM HEPES, pH 7.9, 10 mM MgSO$_4$, 1 mM EDTA, pH 8.2 and 0.1% prionex). This 10 ng/μl trypsin solution was serially diluted 5 fold to 2 ng, 0.4 ng, 0.08 ng, 0.016 ng, 3.2 pg, 0.64 pg, 0.128 pg, 0.0256 pg and 0.005 pg. The trypsin dilutions were added to two 96-well plates in replicates of 8 at 50 μl per well. Pipette tips were changed for each row to avoid enzyme carryover. Two columns (16 wells) contained buffer only without trypsin.

Figure 3:
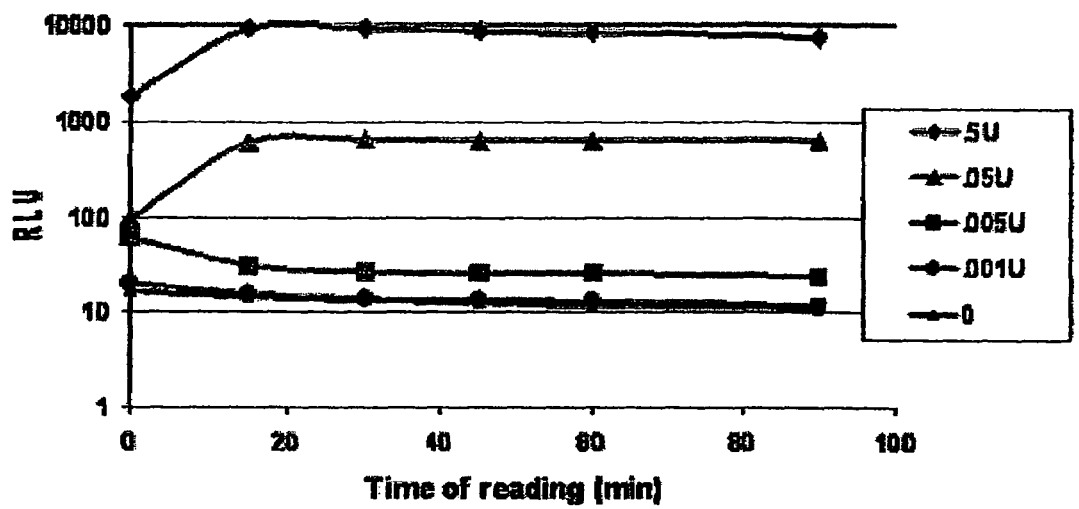
Figure 3:
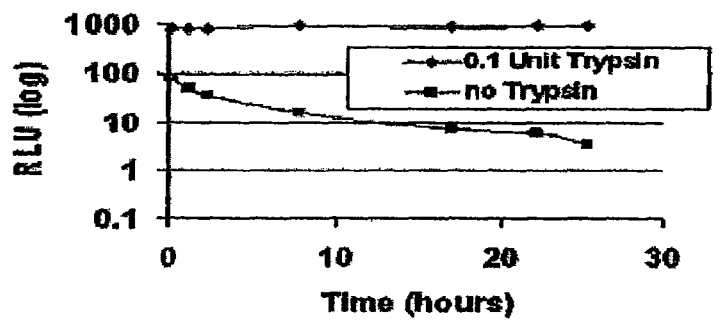

One of the two plates of the trypsin dilutions was then used to test the Lys-aminoluciferin substrate (FIG. 3). Samples were tested in quadruplicate. The 10× substrate/luciferase/ATP mix was further diluted 5 fold in the above-described buffer to make a 2× stock. 50 μl of this 2× stock was added to each well containing 50 μl of the trypsin titration such that the final 100 μl volume contained 20 μM Lys-aminoluciferin, 200 μM ATP, and 20 μg/ml of thermostable luciferase in buffer (50 mM HEPES, pH 7.9, 10 mM MgSO$_4$, 1 mM EDTA, pH 8.2 and 0.1% prionex). The substrate mix was also added to 12 of the 16 wells containing buffer only without trypsin. The remaining 4 wells were left with buffer only (no substrate mix). This plate was incubated at room temperature and read by luminometer at 45 minutes and 3 hours after adding the substrate mix to the trypsin.

The second plate of trypsin dilutions was used to test the Arg-Rho-110 substrate (FIG. 4). The Arg-Rho-110 substrate was tested at final concentrations of 10 μM and 2.5 μM. 2× stocks of 20 μM and 5 μM were prepared by diluting the substrate in 50 mM HEPES, pH 7.9, 10 mM MgSO$_4$, 1 mM EDTA, pH 8.2 and 0.1% prionex. To each well of the plate containing 50 μl of the trypsin titration was added 50 μl of either the 20 μM or 5 μM 2× stocks of Arg-Rho-110 substrate.

The 20 μM stock was added to the first four rows (final concentration of 10 μM in rows A-D) and the 5 μM stock was added to the second four rows (final concentration of 2.5 μM in rows E-H). The substrate mix was also added to 12 of the 16 wells containing buffer only without trypsin. The remaining 4 wells were left with buffer only (no substrate mix). The Arg-Rho-110 plate was incubated at room temperature in the dark for 4.5 hours and read on a fluorimeter.

The signal to noise was calculated as signal-background (no trypsin)/S.D. of background. The limit of detection was determined as 3 S.D. above background noise.

Results

A homogeneous format was used for a trypsin assay. The results indicated that the limit of detection using the Lys-aminoluciferin substrate for trypsin is lower than the Arg-Rho-110 substrate. In particular, the Lys-aminoluciferin substrate has a sensitivity 3 to 10 fold greater depending on the time of the reading than the Arg-Rho-110 substrate (FIG. 9). Moreover, the luminescent assay reached a maximum sensitivity in 30 minutes or less and was very stable for extended time periods.

EXAMPLE 2

To determine the effect of an overnight pre-incubation of substrate with luciferase, ATP and buffer prior to adding trypsin, a substrate/luciferase/ATP mix was incubated overnight in the dark, at room temperature. For the Lys-aminoluciferin substrate, the thawed Lys-aminoluciferin substrate (10 mM stock), thermostable luciferase (5.2 mg/ml stock), and ATP (0.1 M stock) were diluted in buffer (50 mM HEPES, pH 7.9, 10 mM $MgSO_4$, 1 mM EDTA, pH 8.2 and 0.1% prionex) to make a stock that was 10× the final concentration. The 10× stock was 200 μM Lys-aminoluciferin, 200 μg/ml luciferase, and 2.0 mM ATP. After overnight incubation, the 10× stock was diluted in buffer to make a 2× stock (40 μM of substrate, 400 μM of ATP and 40 μg/ml of luciferase). The Arg-Rho-110 substrate was also prepared to a 2× working stock concentration of 40 μM from a 5 mM stock.

Trypsin dilutions were prepared from a 1 μg/μl stock and diluted to the same concentrations as in Example 1, and two different plates were set up with 4 wells for each concentration of trypsin, 50 μl per well. Two columns had buffer only without trypsin as a control. Then, 50 μl of the 2× Lys-aminoluciferin substrate mix was added to each well of one plate, and the results were read at several time points on a luminometer. To the second plate, 50 μl of the 2× Arg-Rho-110 stock was added to each well for a final concentration of 20 μM, as in Example 1.

The luminescence-based assay was able to detect as little as 3.0 pg of trypsin, while the fluorescence-based assay had a limit of detection of about 12-30 pg (4-10 times less enzyme).

EXAMPLE 3

To conduct a direct comparison between luminescent and fluorescent substrates for caspase 3, DEVD-Rho-110 and DEVD-aminoluciferin were employed. The DEVD-aminoluciferin substrate/luciferase/ATP mixture was prepared first and preincubated prior to the enzyme assay to eliminate free aminoluciferin. To 1.25 ml of Apo-ONE™ buffer (Promega) was added 10 μl of DEVD-luciferin (10 mM stock), 10 μl of ATP (0.1 M stock), 50 μl of $MgSO_4$ (1 M stock), 50 μl of prionex (10% stock), and 48 μl of luciferase (5.2 mg/ml stock). The volume was brought up to 2.5 ml with nanopure, autoclaved water to make a 2× stock of 40 μM DEVD-luciferin, 400 μM ATP, 0.2% prionex, and 100 μg/ml luciferase. This stock was incubated overnight at room temperature.

Caspase (Upstate Biotech, Cat. No. 14-264; approximately 10 mU/ng protein with >75% in active conformation) was diluted 550 fold in a 50/50 mixture of Apo-ONE™ buffer/RPMI-1640 culture media, from 1 U/μl to 1.8 mU/μl. 50 μl of Apo-One™ buffer/RPMI-1640 media was added to each well in two 96-well plates. Then, 5.5 μl of the caspase stock was added to the 50 μl of Apo-One™ buffer/RPMI-1640 media for a concentration of about 10 mU/50 μl. Ten serial dilutions of 10 fold each were carried out in the wells by serially transferring 5.5 μl of caspase solution into the 50 μl of the buffer/media mix. The final caspase concentrations were 10 mU, 1 mU, 0.1 mU, 0.01 mU, 0.001 mU, 0.1 μU, 0.01 μU, 0.001 μU, 0.1 nU, and 0.01 nU/well. The last two columns were buffer/media only without caspase.

To one plate of caspase dilutions, 50 μl of the DEVD-aminoluciferin substrate mixture was added to each well for final concentrations of 20 μM DEVD-aminoluciferin, 200 μM ATP, 10 mM $MgSO_4$, 0.1% prionex, and 50 μg/ml luciferase. To the other plate, 50 μl of the DEVD-Rho-110 substrate was added to each well at the recommended final concentration of 50 μM. Readings were taken for each plate at 1 hour, 3 hours, and 5 hours on a luminometer and fluorimeter, respectively.

Signal to noise was calculated as above and the limit of detection was determined as 3 S.D. above the background noise.

As in the case of the trypsin-substrate modified luciferin, DEVD-aminoluciferin was 10-100 times more sensitive than DEVD-Rho-110 (FIG. 10). The fluorescent ratio assay required several hours for maximum sensitivity and was always changing over time. Moreover, the fluorescent assay lost linearity at low caspase concentrations.

The luminescent assay is a rate assay that is not dependent on the accumulation of cleaved substrate. Therefore, steady-state (protease cleavage versus luciferase consumption of aminoluciferin) is reached rapidly and this steady-state is stable for several hours. Moreover, linearity is also maintained for several hours. The luminescent assay reached a maximum sensitivity in 30 minutes or less and was very stable for extended time periods. The luminescent assay was linear over 3-4 logs at low caspase concentration (FIG. 8).

EXAMPLE 4

The DEVD-aminoluciferin caspase substrate and the DEVD-Rho-110 caspase substrate were used to measure caspase activity in Jurkat cells induced to undergo apoptosis with anti-FAS antibody. DEVD-luciferin and luciferase were prepared for pre-incubation prior to use in the assay. Substrate, ATP, $MgSO_4$, prionex and luciferase were diluted from the same stock as in Example 3 to the same 2× concentration, except that the components were diluted in autoclaved water rather than Apo-ONE™. This mixture was incubated overnight in the dark (covered in foil).

The next day, Jurkat cells, grown in RPMI-1640 media with 10% Fetal Bovine Serum (FBS) to a density of $5 \times 10^5$ cells/ml, were treated with anti-FAS antibody. To one vial of 8 ml of media was added 1.6 μl of antibody (1:5000 dilution); a second vial contained 8 ml of media and no antibody. Cells were incubated for 4 hours at 37° C., in 5% $CO_2$. Cells were then centrifuged and resuspended in 12.5 ml of RPMI-1640 to a density of $3.2 \times 10^5$ cells/ml, then diluted 1:1 with Apo-ONE™ buffer for $1.6 \times 10^5$ cells/ml, or 8,000 per 50 μl.

Two 96-well plates were prepared such that on each, the first column was left empty, and 50 μl of RPMI-1640:Apo-ONE™ solution was placed in each of the remaining wells. To the first four rows of each plate, 100 μl of the "induced" cell solution (8,000 cells) was added and the cells then serially diluted from 8,000 cells/well, to 4,000 cells/well and so on, down to 7.8 cells/well. The twelfth column was left without cells and with only 50 μl of RPMI-1640:Apo-ONE™ solution. The next four rows on each plate were likewise treated with 100 μl of the "uninduced" cell solution, and then likewise serially diluted to 7.8 cells/well. Again, the last column of those four rows was left with media alone (no cells).

Signal to noise was calculated (signal minus background (no cell control)/S.D. of background) and the limit of detection was determined as 3 S.D. above the background noise.

One of the two plates was treated with 50 μl of either DEVD-aminoluciferin/luciferase mix or with DEVD-Rho-110/Apo-ONE™ (Promega G778B and G777B). Each plate was mixed on a plate shaker for 30 seconds then incubated at room temperature and read on either a Dynex luminometer or Fluoroskan plate reader at 1 hour, 2 hours, 4 hours and one day later.

The aminoluciferin substrate assay showed that the assay detects caspase positive cells in a well having 15 cells in as little as 1 hour, and that the assay remains linear at the 4 hour time point (FIG. 11). On the other hand, the DEVD-Rho-110 substrate assay had a limit of detection of 150 cells/well at 1 hour, and about 30 cells at 4 hours.

EXAMPLE 5

To evaluate different assay component formulations for caspase-3 activity and to compare sensitivities of DEVD-aminoluciferin to DEVD-Rho-110 in those formulations, two stock solutions were prepared. As above, the DEVD-aminoluciferin/luciferase mixture is prepared and allowed to incubate overnight. One stock solution included a 1% solution of CHAPS buffer (Sigma, Catalog No. C-5070) and the other a 1% solution of Thesit (Pragmatics, Inc., Catalog No. S-22#9). The buffer formulations were as follows: 100 μl of HEPES (1 M stock, 50 mM final concentration), 10 μl of $CaCl_2$ (1 M stock, 5 mM final concentration), 30 μl of $MgSO_4$ (1 M stock, 15 mM final concentration), 8 μl of ATP (0.1 M stock, 400 μM final concentration), 8 μl of DEVD-aminoluciferin (10 mM stock, 40 μM final concentration), 38.4 μl of luciferase (5.2 mg/ml stock, 100 μg/ml final concentration) and 20 μl of prionex (10% stock, 0.1% final concentration) were combined in each of 2 tubes. Finally, 200 μl of either CHAPS or Thesit (1% stock, 0.1% final concentration) was added to one of the tubes. This was incubated overnight. The next day, 40 μl of DTT (Promega, catalog no. V3151) (1 M stock, 20 mM final concentration) was added to each tube (CHAPS and Thesit). Finally, 1545.6 μl of pure, autoclaved water was added for a final volume of 2 ml per solution.

Caspase (Upstate Biotech, Cat. No. 14-264) was diluted from 1 U/μl stock to 1 mU per 50 μl, or 8 mU in 400 μl of buffer (see below). The caspase buffer was as follows: HEPES, CHAPS or Thesit, $CaCl_2$, $MgSO_4$, DTT and prionex, all in the same final concentrations as described above. The caspase was serially diluted by factors of 10, from 1 mU through $1\times10^{-8}$ mU to a final volume of 440 μl of each dilution. 50 μl of each of these dilute caspase solutions were added to each of 3 wells on each of two 96 well plates. Three columns of wells were left blank.

To one plate, 50 μl of DEVD-aminoluciferin/luciferase was added to each of the 6 wells containing each dilution (both CHAPS and Thesit treated). To the second plate, 50 μl of DEVD-Rho-110 substrate was added to each of the 6 wells containing each dilution (both CHAPS and Thesit treated). The plates were read at various times on a luminometer (Dynex) or a fluorimeter (Fluoroskan).

The limit of detection for the aminoluciferin was in the range of 0.2 μU of caspase in buffer containing either CHAPS or Thesit (FIG. 12). On the other hand, the limit of detection using the rhodamine-based substrate was 2-6 μU (a factor of 10-30).

EXAMPLE 6

Representative compounds of the invention were prepared according to the following non-limiting examples.

General Synthetic Procedures

All reactions were run under positive pressure of dry nitrogen gas. Reactions requiring anhydrous conditions were performed in oven-dried glassware that was cooled under nitrogen gas or a dessicator. Anhydrous solvents and reagent solutions were transferred using oven-dried syringes. Tetrahydrofuran (THF), dichloromethane, pyridine, acetonitrile, and dimethylformamide (DMF) were obtained as anhydrous solvent and were used without further purification. Reagent grade solvents were used for chromatography without further purification.

TLC was performed on 0.2 mm EM Science precoated silica gel 60 $F_{254}$ TLC plates (5×20 cm aluminum sheets). Flash chromatography was performed using Selecto Scientific 32-63 μm silica gel (60 $F_{254}$).

Analytical Reverse-phase HPLC was performed using a Synergi 4μ Max-RP column, 4.6 mm×50 mm, on Beckman System Gold 126 pump systems equipped with a Model 168 diode-array detector and Model 507 autosampler. The solvents were: A—10 mM sodium phosphate buffer (pH 7.0) and B—methanol. All analytical reverse-phase chromatograms were monitored at 254 nm and 315 nm.

ESI Mass spectra were recorded on a FISONS VG Platform Electrospray Mass Spectrometer. The NMR spectra of all the compounds conformed to their respective structures.

Nmr spectra were obtained on a Varian 300 Mhz spectrometer.

EXAMPLE 7

Preparation of N-(Z-DEVD)-aminoluciferin

To a 25 mL flask containing N-[Z-Asp(OtBu)-Glu(OtBu)-Val-Asp(OtBu)]-aminoluciferin (20 mg, 0.019 mmol) was added 2 mL of a solution of 20% trifluoroacetic acid in dichloromethane. The reaction mixture was stirred at room temperature for 4 h. HPLC indicated the reaction was progressing slowly. Additional trifluoroacetic acid was added to make a 30% solution of trifluoroacetic acid in the reaction mixture and the reaction was left standing in a 5° C. refrigerator overnight. The next day HPLC analysis indicated the reaction was complete. The reaction mixture was concentrated to a creamy solid residue. The crude product was purified by HPLC chromatography on a Synergi 4 u Max-RP semi-preparative column using 20 mM ammonium acetate buffer (pH 6.5) and methanol. Fractions containing product were pooled and lyophilized to afford 10.3 mg (62%) of N-(Z-Asp-Glu-Val-Asp)-aminoluciferin as an off-white powder.

The intermediate N-[Z-Asp(OtBu)-Glu(OtBu)-Val-Asp (OtBu)]-aminoluciferin was prepared as follows.

a. Synthesis of Asp(OtBu)-OH. Fmoc-Asp(OtBu)-OH (500 mg, 1.2 mmole) was dissolved in a 9:1 mixture of dichloromethane-piperidine (5 mL) in a 25 mL round-bottomed flask. The reaction mixture was stirred overnight at room temperature. The next morning, TLC analysis indicated complete Fmoc deprotection. The reaction mixture was concentrated by rotoevaporation, coevaporated 2 times with toluene, and dried under vacuum to give a crude oil. This oil was purified by flash chromatography on silica gel (50 g) using a stepwise solvent gradient of 10%-50% methanol in dichloromethane to afford 250 mg (100%) of Asp(OtBu)-OH.

b. Synthesis of Fmoc-Val-Asp(OtBu)-OH. Asp(OtBu)-OH (250mg, 1.3 mmol) was dissolved in 40 mL of a 1:1 mixture of dichloromethane and pyridine in a 100 mL round-bottomed flask with magnetic stirring. To this solution was added Fmoc-Val-OSu (690 mg, 1.58 mmole) and stirring continued overnight under nitrogen atmosphere at ambient temperature. The next morning the reaction was concentrated by rotoevaporation to a pale yellow oil, which was dissolved in dichloromethane and washed twice with 10% aqueous citric acid solution. The aqueous layer was extracted again with dichloromethane, and the combined organic layer was dried with anhydrous sodium sulfate and concentrated by rotoevaporation to give 820 mg of crude white foam. This material was purified by flash chromatography on silica gel using a step-wise solvent gradient of 3%-20% methanol in dichloromethane to afford 250 mg (38%) of Fmoc-Val-Asp(OtBu)-OH as an off-white solid.

c. Synthesis of Val-Asp(OtBu)-OH. Fmoc-Val-Asp(OtBu)-OH (250 mg, 0.57 mmole) was dissolved in 10 mL of a 9:1 mixture of piperidine-dichloromethane in a 50 mL round-bottomed flask, and the reaction mixture was allowed to stand at ambient temperature. After 1 h TLC analysis indicated the reaction was complete. The reaction mixture was concentrated, coevaporated twice with 20 mL of toluene, and dried under vacuum to provide 250 mg of a crude white residue. This residue was purified by flash chromatography on silica gel (25 g) using a step-wise solvent gradient of 20%-75% methanol in dichloromethane to afford 120 mg (76%) of pure Val-Asp(OtBu)-OH.

d. Synthesis of Z-Asp(OtBu)-Glu(OtBu)-OH. To a stirred suspension of Glu(OtBu)-OH in dichloromethane (5 mL) and pyridine (3 mL) in a 25 mL round-bottomed flask was added Z-Asp(OtBu)-Osu (530 mg, 1.26 mmol). The resulting mixture was stirred at room temperature for two days. The reaction mixture was concentrated by rotoevaporation and the residue was partitioned between ethyl acetate and 10% aqueous citric acid solution. The aqueous phase was extracted three times with ethyl acetate. Combined extracts were dried over sodium sulfate and concentrated by rotoevaporation to give a crude oil that was purified by flash chromatography on silica gel (75 g) using a stepwise solvent gradient of 2%-4% methanol in dichloromethane. Fractions containing product were pooled and concentrated by rotoevaporation to give 630 mg (98%) of Z-Asp(OtBu)-Glu(OtBu)-OH as an off-white solid foam.

e. Synthesis of ZAsp(OtBu)-Glu(OtBu)-Val-Asp(OtBu)-OH. To a stirred solution of Z-Asp(OtBu)-Glu(OtBu)-OH (245 mg, 0.48 mmol) in dichloromethane (20 mL) in a 100 mL round-bottomed flask was added N-hydroxysuccinimide (60.9 mg, 0.53 mmole) followed by dicyclohexylcarbodiimide (109.2 mg., 0.53 mmol), and the resulting cloudy mixture was allowed to stir for 1 h at ambient temperature under nitrogen atmosphere. After TLC analysis showed the reaction was complete, the dicyclohexylurea precipitate was removed by filtration and the filtrate was concentrated by rotoevaporation to about 7 mL, at which point some precipitation began to occur. This mixture was added to a stirred solution of Asp(OtBu)-Val-OH (120 mg., 0.437 mmol) in DMF (20 mL) in a 50 mL round-bottomed flask. After the reaction was stirred 2 h at ambient temperature, TLC analysis indicated the reaction was proceeding slowly, and the hazy mixture was then concentrated to about 15 mL and stirring was continued overnight. The next morning, TLC analysis showed the reaction was not yet complete. The reaction flask was fitted with a condenser and the mixture was then heated at 35-38° C. using a water bath for 1.5 h, during which time the mixture clarified somewhat. The reaction was cooled and concentrated by rotoevaporation to a residue, which was suspended in ethyl acetate (50 mL) and washed twice with 10 mL of 10% aqueous citric acid solution. The organic layer was then washed twice with 10 mL of water, and the water layer was back-extracted with ethyl acetate. The organic layers were combined, dried over anhydrous sodium sulfate, concentrated by rotoevaporation, and coevaporated twice with dichloromethane to afford 500 mg of crude off-white foam. This crude material was purified by flash chromatography on silica gel (25 g) using a step-wise solvent gradient of 5%-20% methanol in dichloromethane to provide 190 mg (56%) of Z-Asp(OtBu)-Glu(OtBu)-Val-Asp(OtBu)-OH as an off-white foam.

f. Synthesis of 6-(Z-Asp(OtBu)-Glu(OtBu)-Val-Asp(OtBu)-amino-2-cyanobenzothiazole. To a stirred solution of of Z-Asp(OtBu)-Glu(OtBu)-Val-Asp(OtBu)-OH (95 mg, 0.112 mmol) in THF (5 mL) cooled in -10° C. bath (sodium chloride-ice) was added via syringe N-methylmorpholine (13.4 µL, 0.122 mmol) and then isobutyl chloroformate (16 µL, 0.122 mmol). The reaction mixture was stirred at −10° C. for 1h and then a solution of 6-amino-2-cyanobenzothiazole (27.9 mg, 0.159 mmol) in THF (2 mL) was added via pipet. The cooling bath was removed and the reaction mixture was allowed to warm to room temperature and stir for 2 days. TLC analysis indicated a new product was generated. The reaction mixture was concentrated by rotoevaporation to give a crude residue that was dissolved in ethyl acetate and washed twice with water. The aqueous phase was extracted again with ethyl acetate. Combined extracts were dried and concentrated to give 104 mg of crude yellow residue that was purifies by flash chromatography on silica gel (10 g) using a stepwise solvent gradient of 4%-7% acetone in dichloromethane to provide 44 mg (42%) of 6-(Z-Asp(OtBu)-Glu(OtBu)-Val-Asp(OtBu)-amino-2-cyanobenzothiazole as a yellow solid.

g. Synthesis of N-[Z-Asp(OtBu)-Glu(OtBu)-Val-Asp(OtBu)]-aminoluciferin. To a 50 mL round-bottomed flask was added D-cysteine hydrochloride (997 mg, 5.68 mmol) and deionized water (14 mL, degassed with bubbling nitrogen for 15 min). The resulting mixture was magnetically stirred under nitrogen atmosphere until dissolution was achieved. To a separate 25 mL erlenmeyer flask was added anhydrous potassium carbonate (785 mg, 5.68 mmol) and degassed deionized water (14 mL). The resulting solution was added in portions via pasteur pipet to the flask containing the D-cysteine solution, with periodic addition of 6N hydrochloric acid as needed to maintain a pH less than 7.0. After addition of the potassium carbonate solution to the reaction flask was complete, a portion of the reaction mixture (0.24 mL, containing approximately 0.047 mmoles of D-cysteine) was measured (via pipet) and transferred to a separate 5 mL reaction vial. A solution of 6-(Z-Asp(OtBu)-Glu(OtBu)-Val-Asp(OtBu)-amino-2-cyanobenzothiazole (44 mg, 0.047) in methanol (1 mL) was then added to the 5 mL reaction vial, followed by addition of 0.1 M hydrochloric acid solution as needed to maintain the pH below 7.0. The reaction mixture was stirred at room temperature overnight. HPLC and TLC analysis indicated consumption of starting materials. The reaction mixture was concentrated by rotoevaporation and coevaporated with acetonitrile to give a solid residue. The crude product was chromatographed on silica gel (10 g) using a stepwise solvent gradient of 10%-12% methanol in dichloromethane to afford 20 mg (41%) of N-[Z-Asp(OtBu)-Glu (OtBu)-Val-Asp(OtBu)]-aminoluciferin as an off-white solid.

EXAMPLE 8

Preparation of racemic N-Fmoc-aminoluciferin

2-[6'-(9-fluorenylmethoxycarbonyl)amino-2'-benzothiazolyl]-$\Delta^2$-thiazoline-4-carboxylic acid (N-Fmoc-aminoluciferin). To a 100 mL round-bottomed flask were added N-trifluoroacetyl-aminoluciferin (660 mg, 1.76 mmol) and a solution of methanolic ammonia (30 mL of a 7 M solution, 210 mmol). The resulting mixture was left standing at room temperature for 4 days. The reaction mixture was concentrated by rotoevaporation and then coevaporated with dichloromethane to give 626 mg of a crude brown solid residue that was used in the next step without purification. A portion of the crude brown solid residue (391 mg) was dissolved in methanol (40 mL) and water (2 mL) in a 100 mL round-bottomed flask. To this solution was added Fmoc-Cl (435 mg, 1.68 mmol) and the reaction mixture was stirred at room temperature for 2 h. The reaction mixture was concentrated by rotoevaporation and coevaporated with acetonitrile and then dichloromethane to afford a brown foam after drying under vacuum. The product was purified by flash chromatography on 3 successive silica gel columns using 100 g for the first 2 columns and 150 g for the third. The eluting solvent for the first column was 98:2 dichloromethane-methanol. The eluting solvent for the second column was 93:7 dichloromethane-methanol. The eluting solvent for the third column was 97:3 dichloromethane-methanol. Fractions containing product were combined and concentrated to provide 280 mg of waxy product that was 95% pure and 320 mg of product that was 89% pure. The 280 mg of waxy material was re-purified on 25 g of silica gel using 4:1 dichloromethane-methanol to give 108 mg of dry pale yellow solid. The 320 mg portion of product was combined with 230 mg of material recovered from combined impure fractions from the 3 columns described above. This combined material (550 mg) was re-purified by flash chromatography on silica gel (50 g) using 78:22 dichloromethane-methanol to afford 223 mg of product. Total product thus obtained was 380 mg of amber solid that was 95% pure by HPLC analysis. MS (ESI$^-$) m/z 500 (M-H)$^-$, 456 (M—H—CO$_2$)$^-$.

The intermediate compound N-trifluoroacetyl-aminoluciferin was prepared as follows.

a. Preparation of 2-(6'-Trifluoroacetylamino-2'-benzothiazolyl)-$\Delta^2$-thiazoline-4-carboxylic acid (N-Trifluoroacetyl-aminoluciferin). To a 50-mL round-bottomed flask was added D, L-cysteine (688 mg, 5.68 mmol) and deionized water (14 mL, degassed with bubbling nitrogen for 15 min). The resulting mixture was magnetically stirred until dissolution was achieved. To a separate 25-mL erlenmeyer flask was added anhydrous potassium carbonate (785 mg, 5.68 mmol) and degassed deionized water (14 mL). The resulting solution was added in portions via pasteur pipet to the flask containing the D, L-cysteine solution, with periodic addition of 6N hydrochloric acid as needed to maintain a pH less than 7.5. After addition of the potassium carbonate solution to the reaction flask was complete, a portion of the reaction mixture (10.1 mL, containing approximately 2.04 mmoles of D, L-cysteine) was measured (via graduated cylinder) and transferred to a separate 50 mL erlenmeyer flask. This mixture was diluted with 15 mL of degassed methanol and the resulting solution was transferred to a 100 mL round-bottomed flask containing a solution of 2-cyano-6-trifluoroacetylaminobenzothiazole (White et al., 1966) (552 mg, 2.04 mmol) in degassed methanol (17 mL). The reaction mixture was magnetically stirred at room temperature and the reaction flask was covered with aluminum foil. After stirring for 1 h, TLC and HPLC analysis indicated only traces of starting material remaining. The reaction mixture was diluted with water (79 mL) and the pH was found to be ~8.0. The reaction mixture was transferred to a separatory funnel (250 mL) and extracted with ethyl acetate (79 mL) to remove neutral organic compounds. The aqueous phase was acidified to pH 2 by addition of 6N hydrochloric acid, resulting in a sticky off-white precipitate that was stored overnight at 5° C. The suspension was transferred to 50-mL centrifuge tubes and centrifuged for about 3 min. The supernatant was decanted and the pellet was washed with cold water and centrifuged three times. The pellet was suspended in methanol and transferred to a 250 mL round-bottomed flask. The suspension was concentrated by rotoevaporation and then coevaporated with dichloromethane to afford a crude pale yellow solid. The crude product was purified by flash chromatography on 24 g of silica gel using 9:1 dichloromethane-methanol as eluting solvent. A second chromatography column was required and employed 100 g of silica gel and 9:1 dichloromethane-methanol as eluting solvent, providing 660 mg (86%) of a pale yellow solid. MS (ESI$^-$) m/z 375 (M-H)$^-$.

REFERENCES

Fernandes-Alnemri et al., *PNAS USA*, 93: 7464 (1996).
Garcia-Calvo et al., *Cell Death Diff.*, 6: 362 (1999).
Masuda-Nishimura et al., *Letters in Applied Microbio.*, 30: 130 (2000).
Miska et al., *Biol. Chem. Hoppe-Sexler*, 369: 407 (1985).
Miska et al., *J. Clin. Chem. Clin. Biochem.*, 25: 23 (1987).
Monsees et al., *Anal. Biochem.*, 221: 329 (1994).
Monsees et al., *J. Biolum. Chemilum.*, 10: 213 (1995).
Nicholson et al., *Nature*, 376: 37 (1995).
Tewari et al., *Cell*, 81: 801 (1995).
Thornberry et al., *Nature*, 356: 768 (1992).
Thornberry et al., *J. Biol. Chem.*, 272: 17907 (1997).
White et al., *J. Am. Chem. Soc.*, 88: 2015 (1966).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A compound comprising aminoluciferin or a carboxy-terminal protected derivative thereof covalently linked via a peptide bond to a substrate for a caspase, wherein the compound is a substrate for a caspase and a prosubstrate for a beetle luciferase, wherein the substrate comprises $X_1$-$X_2$-$X_3$-D, wherein $X_1$ is Y, D, L, V, I, A, W, or P; $X_2$ is V or E; and $X_3$ is any amino acid.

2. The compound of claim 1 wherein the substrate comprises DEVD (SEQ ID NO:1).

3. The compound of claim 1 wherein the substrate comprises YVAD (SEQ ID NO:2).

4. The compound of claim 1 wherein the substrate comprises LEHD (SEQ ID NO:3).

5. The compound of claim 1 wherein $X_3$ is A, V, H, I, or T.

6. The compound of claim 1 which is a carboxy-terminal protected derivative of aminoluciferin.

7. The compound of claim 6 wherein the carboxy-terminus is protected as a ($C_1$-$C_6$)alkyl ester.

8. The compound of claim 6, wherein the carboxy-terminus is protected as a methyl, ethyl, propyl, or tert-butyl ester.

9. The compound of claim 6 wherein the N-terminus of the substrate is modified to prevent degradation by aminopeptidases.

10. The compound of claim 9 wherein the N-terminus of the substrate is modified with an amino protecting group.

11. The compound of claim 9 wherein the carboxy-terminus is protected by coupling to a solid support.

12. The compound of claim 1 wherein the substrate is DEVD (SEQ ID NO:1).

13. The compound of claim 1 wherein the substrate is $X_1$-$X_2$-$X_3$-D, wherein $X_1$ is Y, D, L, V, I, A, W, or P; $X_2$ is V or E; and $X_3$ is any amino acid.

* * * * *